United States Patent
Sasaki et al.

(10) Patent No.: US 9,995,233 B2
(45) Date of Patent: Jun. 12, 2018

(54) CONTROL DEVICE FOR INTERNAL COMBUSTION ENGINE

(71) Applicant: Toyota Jidosha Kabushiki Kaisha, Aichi (JP)

(72) Inventors: Takanori Sasaki, Susono (JP); Go Hayashita, Ebina (JP); Yuji Miyoshi, Susono (JP)

(73) Assignee: TOYOTA JIDOSHA KABUSHIKI KAISHA, Aichi (JP)

( * ) Notice: Subject to any disclaimer, the term of this patent is extended or adjusted under 35 U.S.C. 154(b) by 359 days.

(21) Appl. No.: 14/763,592

(22) PCT Filed: Jan. 29, 2013

(86) PCT No.: PCT/JP2013/051910
§ 371 (c)(1),
(2) Date: Jul. 27, 2015

(87) PCT Pub. No.: WO2014/118891
PCT Pub. Date: Aug. 7, 2014

(65) Prior Publication Data
US 2015/0354487 A1   Dec. 10, 2015

(51) Int. Cl.
*F01N 3/00* (2006.01)
*F02D 41/14* (2006.01)
(Continued)

(52) U.S. Cl.
CPC ......... *F02D 41/1444* (2013.01); *F01N 3/225* (2013.01); *F02D 41/0295* (2013.01);
(Continued)

(58) Field of Classification Search
USPC .................. 60/274, 276, 285, 286, 297, 301
See application file for complete search history.

(56) References Cited

U.S. PATENT DOCUMENTS 5,227,975 A * 7/1993 Nakaniwa ........... F02D 41/1474
                                                              123/693
5,758,490 A   6/1998 Maki et al.
(Continued)

FOREIGN PATENT DOCUMENTS

JP   H08-029388 A1   2/1996
JP   H08-232723 A    9/1996
(Continued)

*Primary Examiner* — Binh Q Tran
(74) *Attorney, Agent, or Firm* — Hauptman Ham, LLP

(57) ABSTRACT

A control device for an internal combustion engine, equipped with: an exhaust purification catalyst provided in the exhaust passage of the internal combustion engine and capable of absorbing oxygen; a downstream air-fuel ratio sensor provided downstream from the exhaust purification catalyst in the direction of the exhaust flow; and an engine control device that controls the internal combustion engine in response to the output from the downstream air-fuel ratio sensor. The downstream air-fuel ratio sensor is configured such that the applied voltage for which the output current is zero changes in response to the exhaust air-fuel ratio, and such that when the exhaust air-fuel ratio equals the theoretical air-fuel ratio and the applied voltage in the downstream air-fuel ratio sensor is increased, the output current increases in conjunction therewith. When the air-fuel ratio of the exhaust gas is detected by the downstream air-fuel ratio sensor, the applied voltage in the downstream air-fuel ratio sensor is fixed at a constant voltage, with this constant voltage being a voltage for which the output current is zero when the exhaust air-fuel ratio is a predetermined air-fuel ratio that is leaner than the theoretical air-fuel ratio.

16 Claims, 14 Drawing Sheets

(51) Int. Cl.
  *F01N 3/22* (2006.01)
  *G01N 27/41* (2006.01)
  *F02D 41/02* (2006.01)

(52) U.S. Cl.
  CPC ..... *F02D 41/1402* (2013.01); *F02D 41/1439* (2013.01); *F02D 41/1454* (2013.01); *F02D 41/1456* (2013.01); *F02D 41/1473* (2013.01); *F02D 41/1475* (2013.01); *F02D 41/1477* (2013.01); *G01N 27/41* (2013.01); *F01N 2900/0402* (2013.01); *F01N 2900/0416* (2013.01); *F02D 2041/1422* (2013.01); *F02D 2200/0814* (2013.01)

(56) References Cited

U.S. PATENT DOCUMENTS

| | | | | |
|---|---|---|---|---|
| 5,777,204 | A * | 7/1998 | Abe | F02D 41/068 |
| | | | | 123/694 |
| 6,055,972 | A * | 5/2000 | Fujimoto | G01N 27/4067 |
| | | | | 123/688 |
| 6,289,673 | B1 * | 9/2001 | Tayama | F02D 41/0295 |
| | | | | 60/274 |
| 9,745,911 | B2 * | 8/2017 | Hayashita | F02D 41/1454 |
| 2011/0192146 | A1 | 8/2011 | Sugimoto et al. | |
| 2012/0043205 | A1 * | 2/2012 | Matsuoka | G01N 27/407 |
| | | | | 204/410 |

FOREIGN PATENT DOCUMENTS

| | | |
|---|---|---|
| JP | 2000-356618 A | 12/2000 |
| JP | 2003-329637 A | 11/2003 |
| JP | 2004-316553 A1 | 11/2004 |
| JP | 2005-351096 A | 12/2005 |
| JP | 2011-163229 A | 8/2011 |

* cited by examiner

FIG. 4
(A)
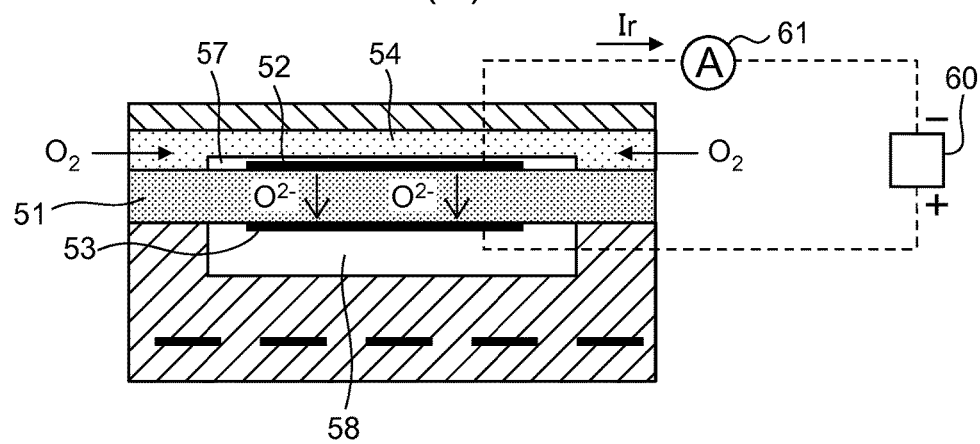
(B)
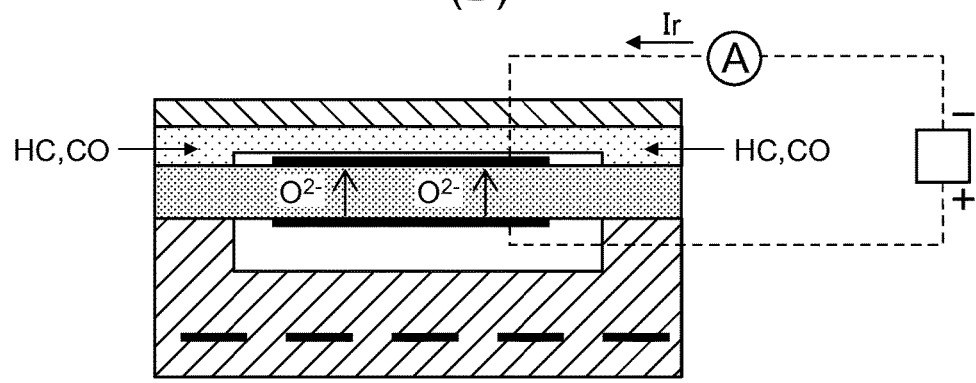
(C)
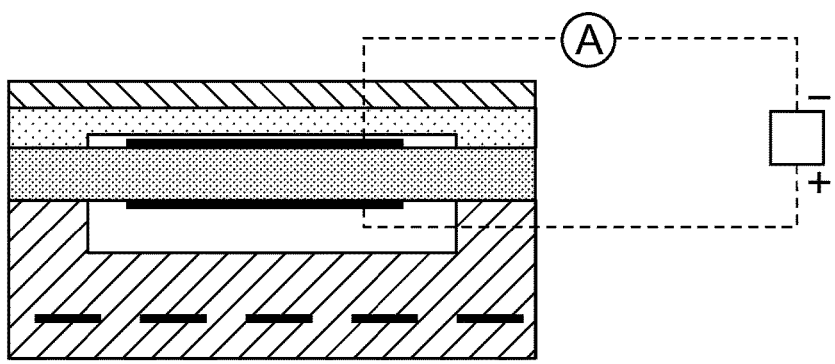

FIG. 10
(A)
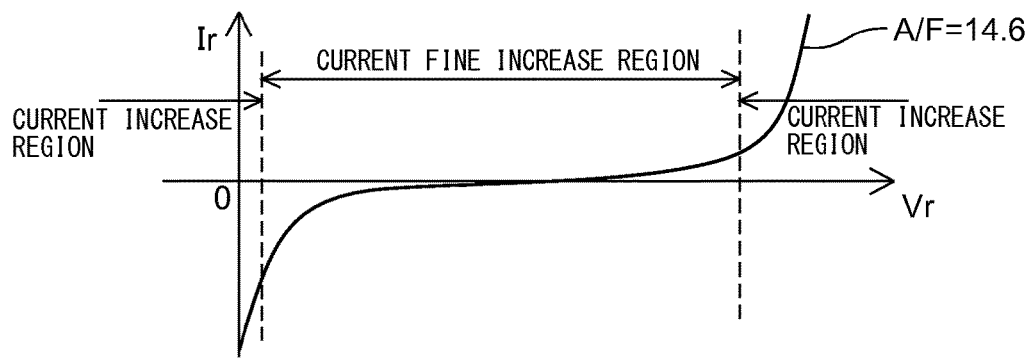
(B)
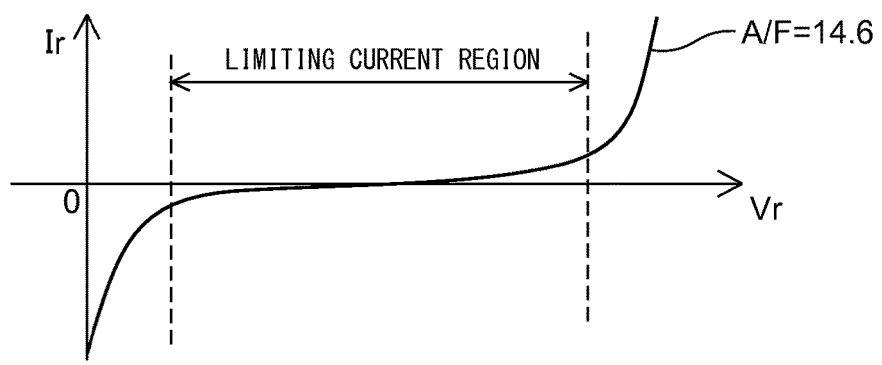
(C)
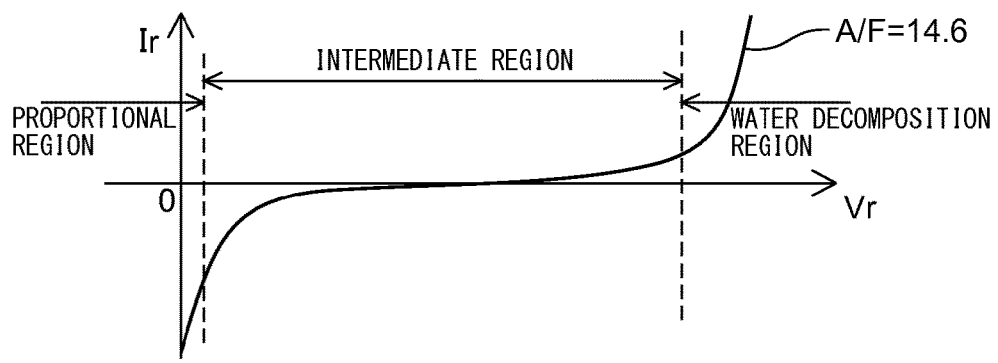

FIG. 13
(A)
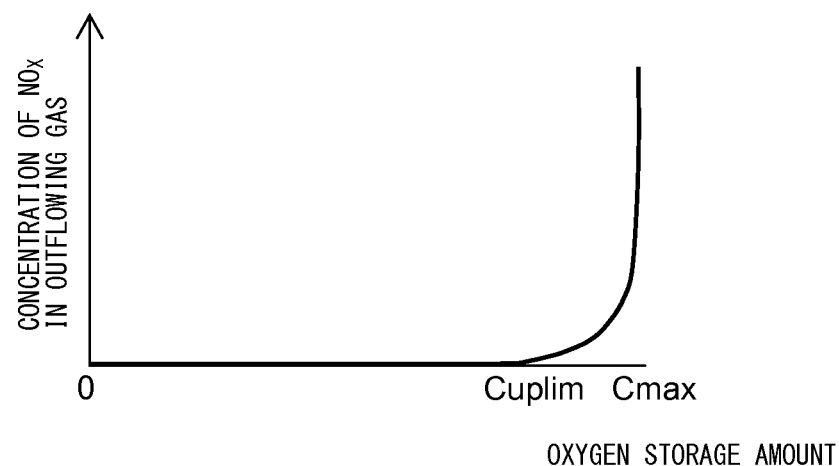
(B)
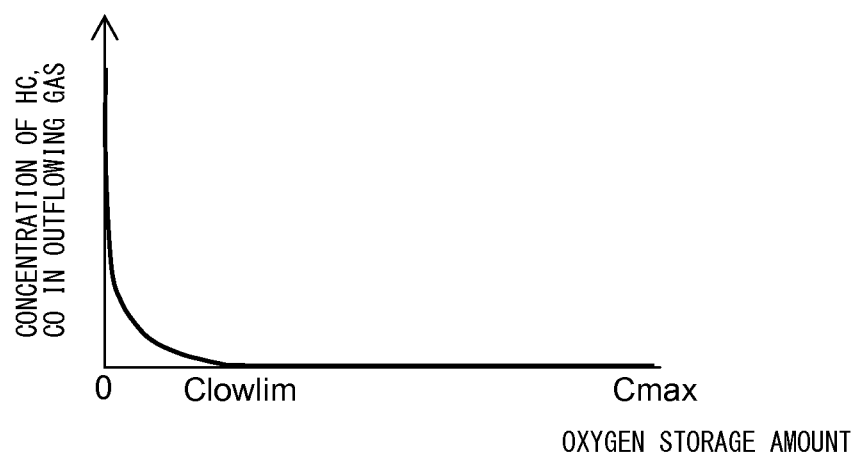

CONTROL DEVICE FOR INTERNAL COMBUSTION ENGINE

CROSS-REFERENCE TO RELATED APPLICATION

This is a national phase application based on the PCT International Patent Application No. PCT/JP2013/051910 filed Jan. 29, 2013, the entire contents of which are incorporated herein by reference.

TECHNICAL FIELD

The present invention relates to a control system of an internal combustion engine which controls an internal combustion engine in accordance with output of an air-fuel ratio sensor.

BACKGROUND ART

In the past, a control system of an internal combustion engine which is provided with an air-fuel ratio sensor in an exhaust passage of the internal combustion engine, and controls an amount of fuel fed to the internal combustion engine based on the output of the air-fuel ratio sensor, has been widely known (for example, see PLTs 1 to 4).

For example, in the control system described in PLT 1, as the air-fuel ratio sensor, a sensor which is provided with: a first electrode which is exposed to exhaust gas flowing through the inside of the exhaust passage; a second electrode which is exposed to the atmospheric air; and a solid electrolyte layer of zirconia, etc., which is arranged between the first electrode and second electrode, has been used. When using this air-fuel ratio sensor to detect the air-fuel ratio of the exhaust gas (below, also referred to as "exhaust air-fuel ratio"), a 0.4V voltage is applied across these electrodes and the current flowing across these electrodes is detected as the output current. Further, based on this output current, the exhaust air-fuel ratio is calculated.

CITATIONS LIST

Patent Literature

PLT 1: Japanese Patent Publication No. 2004-316553A
PLT 2: Japanese Patent Publication No. 2005-351096A
PLT 3: Japanese Patent Publication No. 2003-329637A
PLT 4: Japanese Patent Publication No. H8-232723A
PLT 5: Japanese Patent Publication No. 2000-356618A

SUMMARY OF INVENTION

Technical Problem

In this regard, the air-fuel ratio sensor such as described in PLT 1 is generally configured to have the output characteristic which is shown by the solid line A in FIG. 2. That is, in this air-fuel ratio sensor, the larger the exhaust air-fuel ratio (that is, the leaner), the larger the output current from the air-fuel ratio sensor. In addition, this air-fuel ratio sensor is configured so that the output current becomes zero when the exhaust air-fuel ratio is the stoichiometric air-fuel ratio.

However, the slant in FIG. 2, that is, the ratio of the amount of increase of the output current to the amount of increase of the exhaust air-fuel ratio (below, the "rate of change of output current") is not necessarily the same even if produced through a similar production process. Even with the same model of air-fuel ratio sensors, differences occur between the individual sensors. In addition, even at the same air-fuel ratio sensor, aging, etc., cause the changing rate of output current to change. As a result, even if using the same type of sensors, depending on the sensor used or period of use, etc., as shown in FIG. 2 by the broken line B, the changing rate of output current becomes smaller or, as shown by the one-dot chain line C, the changing rate of output current becomes larger.

For this reason, even when using the same model of air-fuel ratio sensor to measure exhaust gas of the same air-fuel ratio, the output current of the air-fuel ratio sensor will differ depending on the sensor used, the duration of usage, etc. For example, when the air-fuel ratio sensor has the output characteristic such as shown by the solid line A, the output current becomes $I_2$ when measuring exhaust gas with the air-fuel ratio $af_1$. However, when the air-fuel ratio sensor has the output characteristics such as shown by the broken line B and the one-dot chain line C, the output currents become respectively $I_1$ and $I_3$, which are different from the above-mentioned $I_2$, when measuring exhaust gas with the air-fuel ratio $af_1$.

Therefore, in this air-fuel ratio sensor, it is possible to accurately detect the stoichiometric air-fuel ratio and rich and lean with respect to the stoichiometric air-fuel ratio, but when the air-fuel ratio of the exhaust gas is not the stoichiometric air-fuel ratio, the absolute value (that is, rich degree or lean degree) could not be accurately detected.

In particular, the biggest problem in the exhaust gas discharged from an exhaust purification catalyst provided in an exhaust passage of an internal combustion engine is the $NO_X$. For this reason, when the exhaust gas flowing out from the exhaust purification catalyst would contain $NO_X$, that is, when the air-fuel ratio of the exhaust gas flowing out from the exhaust purification catalyst is an air-fuel ratio leaner than the stoichiometric air-fuel ratio (below, called "lean air-fuel ratio"), the absolute value of that has to be accurately detected by the air-fuel ratio sensor provided at the downstream side, in the direction of flow of exhaust, of the exhaust purification catalyst.

Therefore, in consideration of the above problem, an object of the present invention is to provide a control system of an internal combustion engine which uses an air-fuel ratio sensor which can detect the absolute value of the air-fuel ratio of the exhaust gas even if the air-fuel ratio of the exhaust gas is a lean air-fuel ratio.

Solution to Problem

To solve the above problem, in a first aspect of the invention, there is provided a control system of an internal combustion engine comprising: an exhaust purification catalyst which is provided in an exhaust passage of an internal combustion engine and which can store oxygen, a downstream side air-fuel ratio sensor which is provided at a downstream side, in the direction of flow of exhaust, from said exhaust purification catalyst in said exhaust passage, and an engine control device which controls the internal combustion engine in accordance with the output of said downstream side air-fuel ratio sensor, wherein said downstream side air-fuel ratio sensor is configured so that an applied voltage, in which an output current becomes zero, changes in accordance with the exhaust air-fuel ratio and so that when the exhaust air-fuel ratio is a stoichiometric air-fuel ratio, if increasing the applied voltage at said downstream side air-fuel ratio sensor, the output current increases along with that, and when said downstream air-fuel ratio sensor detects the air-fuel ratio of the exhaust gas, the applied voltage at said downstream side air-fuel ratio sensor is fixed to a constant voltage, and said constant voltage is the voltage in which the output current becomes zero when the exhaust air-fuel ratio is an air-fuel ratio which is leaner than the stoichiometric air-fuel ratio.

In a second aspect of the invention, there is provided the first aspect of the invention, wherein said engine control device judges that the exhaust air-fuel ratio is said predetermined air-fuel ratio when the output current of said downstream side air-fuel ratio sensor becomes zero.

In a third aspect of the invention, there is provided the first or second aspect of the invention, further comprising an upstream side air-fuel ratio sensor which is provided at an upstream side, in the direction of flow of exhaust, from said exhaust purification catalyst in said exhaust passage, wherein said engine control device controls the air-fuel ratio of the exhaust gas flowing into said exhaust purification catalyst so that the air-fuel ratio detected by said upstream side air-fuel ratio sensor becomes the target air-fuel ratio.

In a fourth aspect of the invention, there is provided the third aspect of the invention, wherein said upstream side air-fuel ratio sensor is configured so that an applied voltage, in which an output current becomes zero, changes in accordance with the exhaust air-fuel ratio, and so that when the exhaust air-fuel ratio is a stoichiometric air-fuel ratio, if increasing the applied voltage at said upstream side air-fuel ratio sensor increase, the output current increases along with that, and when said upstream air-fuel ratio sensor detects the air-fuel ratio of the exhaust gas, the applied voltage at said upstream side air-fuel ratio sensor is fixed to a constant voltage, and said constant voltage is the voltage in which the output current becomes zero when the exhaust air-fuel ratio is the stoichiometric air-fuel ratio.

In a fifth aspect of the invention, there is provided the third or fourth aspect of the invention, wherein said upstream side air-fuel ratio sensor is configured so that an applied voltage, in which an output current becomes zero, changes in accordance with the exhaust air-fuel ratio, and so that when the exhaust air-fuel ratio is a stoichiometric air-fuel ratio, if increasing the applied voltage at said upstream side air-fuel ratio sensor, the output current increases along with that, and the applied voltage at said downstream side air-fuel ratio sensor is lower than the applied voltage of said upstream side air-fuel ratio sensor.

In a sixth aspect of the invention, there is provided any one of the third to fifth aspects of the invention, wherein said engine control device makes the target air-fuel ratio of the exhaust gas flowing into said exhaust purification catalyst, richer than the stoichiometric air-fuel ratio, when the output current of said upstream side air-fuel ratio sensor becomes zero or more.

In a seventh aspect of the invention, there is provided the sixth aspect of the invention, wherein said engine control device comprises: an oxygen storage amount increasing means for continuously or intermittently making a target air-fuel ratio of exhaust gas flowing into said exhaust purification catalyst leaner than the stoichiometric air-fuel ratio, when the output current of said downstream side air-fuel ratio sensor becomes a value which corresponds to a rich judged air-fuel ratio, which is richer than the stoichiometric air-fuel ratio, or less, until the oxygen storage amount of said exhaust purification catalyst becomes a predetermined storage amount which is smaller than the maximum oxygen storage amount; and an oxygen storage amount decreasing means for continuously or intermittently making said target air-fuel ratio richer than the stoichiometric air-fuel ratio, when the oxygen storage amount of said exhaust purification catalyst becomes said predetermined storage amount or more, so that the oxygen storage amount never reaches the maximum oxygen storage amount but decreases toward zero.

In a eighth aspect of the invention, there is provided the sixth aspect of the invention, wherein said engine control device comprises: an air-fuel ratio lean switching means for making the target air-fuel ratio of the exhaust gas flowing into said exhaust purification catalyst change to a lean set air-fuel ratio which is leaner than the stoichiometric air-fuel ratio, when the output current of said downstream side air-fuel ratio sensor becomes a value which corresponds to a rich judged air-fuel ratio, which is richer than the stoichiometric air-fuel ratio, or less, a lean degree reducing means for making said target air-fuel ratio change to a lean air-fuel ratio with a smaller difference from said stoichiometric air-fuel ratio than the lean set air-fuel ratio, after said air-fuel ratio lean switching means makes said target air-fuel ratio change and before the output current of said downstream side air-fuel ratio sensor becomes zero or more, an air-fuel ratio rich switching means for making said target air-fuel ratio change to a rich set air-fuel ratio which is richer than the stoichiometric air-fuel ratio, when the output current of said downstream side air-fuel ratio sensor becomes zero or more, and a rich degree reducing means for making said target air-fuel ratio change to a rich air-fuel ratio with a smaller difference from said stoichiometric air-fuel ratio than the rich set air-fuel ratio, after said air-fuel ratio rich switching means makes said target air-fuel ratio change and before the output current of said downstream side air-fuel ratio sensor becomes a value which corresponds to said rich judged air-fuel ratio or less.

In a ninth aspect of the invention, there is provided any one of the first to eighth aspects of the invention, wherein said downstream side air-fuel ratio sensor comprises: a first electrode which is exposed through a diffusion regulating layer to exhaust gas for which the air-fuel ratio is to be detected; a second electrode which is exposed to a reference atmosphere, a solid electrolyte layer which is arranged between said first electrode and said second electrode; and a voltage application device which applies voltage across said first electrode and said second electrode, said applied voltage being the voltage which is applied by the voltage application device, said downstream side air-fuel ratio sensor is configured so as to have, for each exhaust air-fuel ratio, a current increase region which is a voltage region where the output current increases along with an increase in the applied voltage; and a current fine increase region which is a voltage region where an amount of increase of the output current with respect to an amount of increase of the applied voltage becomes smaller than said current increase region due to provision of said diffusion regulating layer, and the constant voltage at said downstream side air-fuel ratio sensor is a voltage within said current fine increase region when the exhaust air-fuel ratio is the stoichiometric air-fuel ratio.

In a tenth aspect of the invention, there is provided any one of the first to eighth aspects of the invention, wherein said downstream side air-fuel ratio sensor is configured so as to have, for each exhaust air-fuel ratio, a limit current region which is a voltage region where said output current becomes a limit current, and the constant voltage of said downstream side air-fuel ratio sensor is a voltage within said limit current region when the exhaust air-fuel ratio is the stoichiometric air-fuel ratio.

In a 11th aspect of the invention, there is provided any one of the first to eighth aspects of the invention, wherein said downstream side air-fuel ratio sensor is configured to have, for each exhaust air-fuel ratio, in the relationship between said applied voltage and output current, a proportional region which is a voltage region where the output current increases in proportion to an increase of the applied voltage; a moisture breakdown region which is a voltage region where the output current changes in accordance with a change of the applied voltage due to the breakdown of moisture; and a middle region which is a voltage region between these proportional region and moisture breakdown region, and said constant voltage at the downstream side air-fuel ratio sensor is a voltage within said middle region when the exhaust air-fuel ratio is the stoichiometric air-fuel ratio.

In a 12th aspect of the invention, there is provided any one of the first to eighth aspects of the invention, wherein said constant voltage at the downstream side air-fuel ratio sensor is larger than a voltage in which the output current becomes zero when the exhaust air-fuel ratio is 1% higher than the stoichiometric air-fuel ratio, and is lower than a voltage in which the output current becomes zero when the exhaust air-fuel ratio is the stoichiometric air-fuel ratio.

In a 13th aspect of the invention, there is provided any one of the first to eighth aspects of the invention, wherein said downstream side air-fuel ratio sensor is configured so that, for each exhaust air-fuel ratio, in the relationship between said applied voltage and output current, the output current increases up to a first curved point as the applied voltage increases, the output current increases from the first curved point to a second curved point as the applied voltage increases, the output current increases from the second curved point as the applied voltage increases, and, in the voltage region between the first curved point and the second curved point, the amount of increase of the output current with respect to an amount of increase in the applied voltage becomes smaller than in other voltage regions, and the constant voltage at said downstream side air-fuel ratio sensor is set to a voltage between said first curved point and said second curved point when the exhaust air-fuel ratio is the stoichiometric air-fuel ratio.

In a 14th aspect of the invention, there is provided any one of the first to eighth aspects of the invention, wherein said downstream side air-fuel ratio sensor comprises: a first electrode which is exposed through a diffusion regulating layer to exhaust gas for which the air-fuel ratio is to be detected; a second electrode which is exposed to a reference atmosphere; a solid electrolyte layer which is arranged between said first electrode and said second electrode; and a voltage application device which applies voltage across said first electrode and said second electrode, said diffusion regulating layer being formed by alumina, said applied voltage being the voltage which is applied by the voltage application device, and said constant voltage at said downstream side air-fuel ratio sensor is set to voltage not lower than 0.1V and lower than 0.45V.

In a 15th aspect of the invention, there is provided any one of the third to eighth aspects of the invention, wherein said upstream side air-fuel ratio sensor comprises: a first electrode which is exposed through a diffusion regulating layer to exhaust gas for which the air-fuel ratio is to be detected; a second electrode which is exposed to a reference atmosphere; a solid electrolyte layer which is arranged between said first electrode and said second electrode; and a voltage application device which applies voltage across said first electrode and said second electrode, said diffusion regulating layer being formed by alumina, said applied voltage being the voltage which is applied by the voltage application device, and said constant voltage at said upstream side air-fuel ratio sensor is set to a voltage not lower than 0.4V and not higher than 0.45V.

In a 16th aspect of the invention, there is provided any one of the first to 15th aspects of the invention, wherein said downstream side air-fuel ratio sensor comprises: a first electrode which is exposed through a diffusion regulating layer to exhaust gas for which the air-fuel ratio is to be detected; a second electrode which is exposed to a reference atmosphere; a solid electrolyte layer which is arranged between said first electrode and said second electrode; a voltage application device which applies voltage across said first electrode and said second electrode; and a current detection device which detects the current flowing across said first electrode and said second electrode, said applied voltage being the voltage which is applied by the voltage application device, and said output current being the current which is detected by said current detection device.

Advantageous Effects of Invention

According to the present invention, a control system of an internal combustion engine using an air-fuel ratio sensor, which can detect an absolute value of the air-fuel ratio of the exhaust gas even if the air-fuel ratio of the exhaust gas is a lean air-fuel ratio, is provided.

BRIEF DESCRIPTION OF DRAWINGS

FIG. 4 is a view which schematically shows an operation of an air-fuel ratio sensor.

FIG. 10 shows the relationship between the sensor applied voltage of the air-fuel ratio sensor and the output current.

FIG. 13 is a view which shows the relationship between the oxygen storage amount of an exhaust purification catalyst and a concentration of $NO_X$ or unburned gas in exhaust gas flowing out from an exhaust purification catalyst.

DESCRIPTION OF EMBODIMENTS

Figure 1:
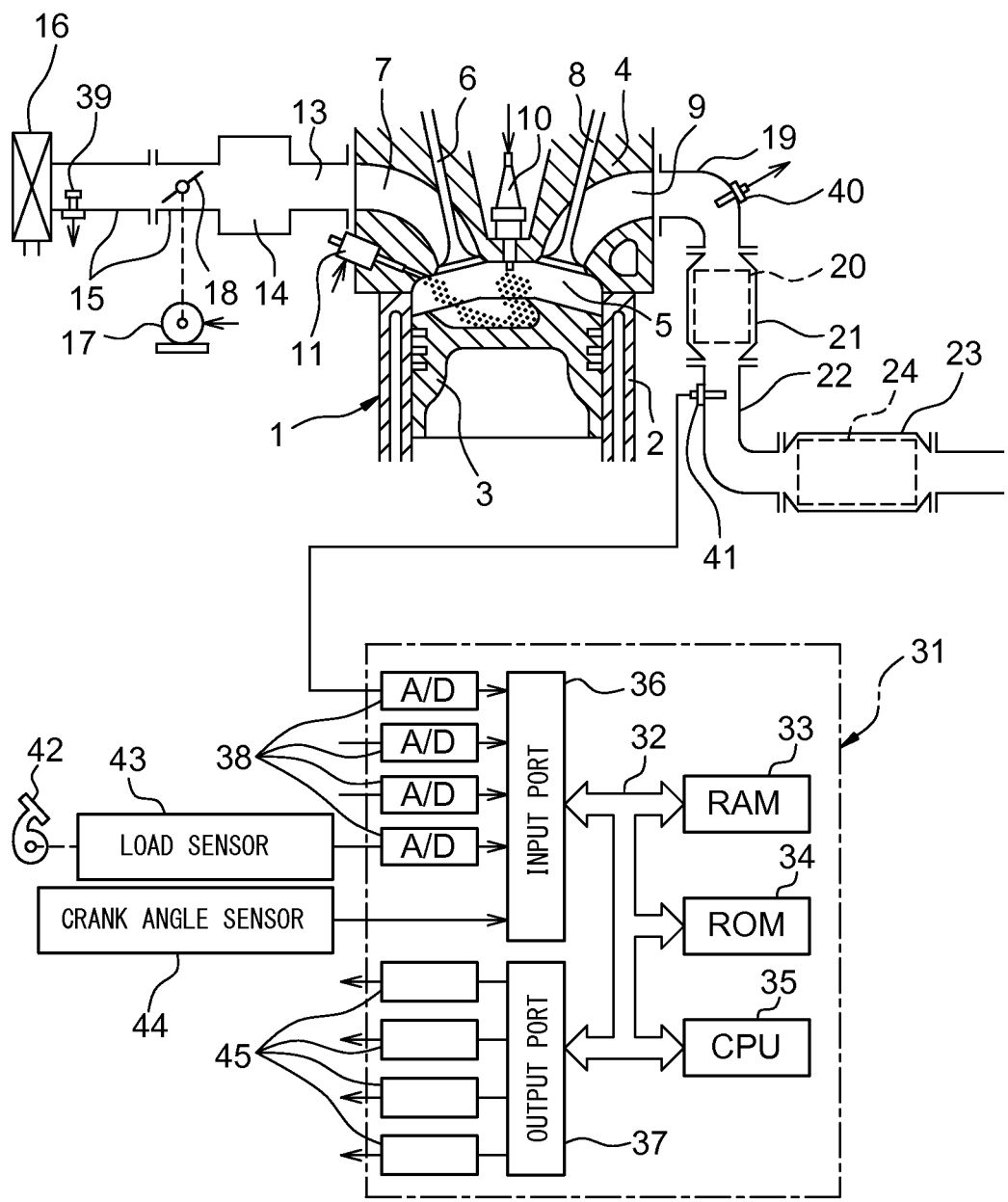
FIG. 1 is a view which schematically shows an internal combustion engine in which a control system of the present invention is used.

Below, referring to the drawings, a control device of an internal combustion engine of the present invention will be explained in detail. Note that, in the following explanation, similar component elements are assigned the same reference numerals. FIG. 1 is a view which schematically shows an internal combustion engine in which a control device according to a first embodiment of the present invention is used.

<Explanation of Internal Combustion Engine as a Whole>

Referring to FIG. 1, 1 indicates an engine body, 2 a cylinder block, 3 a piston which reciprocates inside the cylinder block 2, 4 a cylinder head which is fastened to the cylinder block 2, 5 a combustion chamber which is formed between the piston 3 and the cylinder head 4, 6 an intake valve, 7 an intake port, 8 an exhaust valve, and 9 an exhaust port. The intake valve 6 opens and closes the intake port 7, while the exhaust valve 8 opens and closes the exhaust port 9.

As shown in FIG. 1, a spark plug 10 is arranged at a center part of an inside wall surface of the cylinder head 4, while a fuel injector 11 is arranged at a side part of the inner wall surface of the cylinder head 4. The spark plug 10 is configured to generate a spark in accordance with an ignition signal. Further, the fuel injector 11 injects a predetermined amount of fuel into the combustion chamber 5 in accordance with an injection signal. Note that, the fuel injector 11 may also be arranged so as to inject fuel into the intake port 7. Further, in the present embodiment, as the fuel, gasoline with a stoichiometric air-fuel ratio of 14.6 at an exhaust purification catalyst is used. However, the internal combustion engine of the present invention may also use another fuel.

The intake port 7 of each cylinder is connected to a surge tank 14 through a corresponding intake branch pipe 13, while the surge tank 14 is connected to an air cleaner 16 through an intake pipe 15. The intake port 7, intake branch pipe 13, surge tank 14, and intake pipe 15 form an intake passage. Further, inside the intake pipe 15, a throttle valve 18 which is driven by a throttle valve drive actuator 17 is arranged. The throttle valve 18 can be operated by the throttle valve drive actuator 17 to thereby change the aperture area of the intake passage.

On the other hand, the exhaust port 9 of each cylinder is connected to an exhaust manifold 19. The exhaust manifold 19 has a plurality of branch pipes which are connected to the exhaust ports 9 and a header at which these branch pipes are collected. The header of the exhaust manifold 19 is connected to an upstream side casing 21 which houses an upstream side exhaust purification catalyst 20. The upstream side casing 21 is connected through an exhaust pipe 22 to a downstream side casing 23 which houses a downstream side exhaust purification catalyst 24. The exhaust port 9, exhaust manifold 19, upstream side casing 21, exhaust pipe 22, and downstream side casing 23 form an exhaust passage.

The electronic control unit (ECU) 31 is comprised of a digital computer which is provided with components which are connected together through a bidirectional bus 32 such as a RAM (random access memory) 33, ROM (read only memory) 34, CPU (microprocessor) 35, input port 36, and output port 37. In the intake pipe 15, an air flow meter 39 is arranged for detecting the flow rate of air flowing through the intake pipe 15. The output of this air flow meter 39 is input through a corresponding AD converter 38 to the input port 36. Further, at the header of the exhaust manifold 19, an upstream side air-fuel ratio sensor 40 is arranged which detects the air-fuel ratio of the exhaust gas flowing through the inside of the exhaust manifold 19 (that is, the exhaust gas flowing into the upstream side exhaust purification catalyst 20). In addition, in the exhaust pipe 22, a downstream side air-fuel ratio sensor 41 is arranged which detects the air-fuel ratio of the exhaust gas flowing through the inside of the exhaust pipe 22 (that is, the exhaust gas flowing out from the upstream side exhaust purification catalyst 20 and flows into the downstream side exhaust purification catalyst 24). The outputs of these air-fuel ratio sensors 40 and 41 are also input through the corresponding AD converters 38 to the input port 36. Note that, the configurations of these air-fuel ratio sensors 40 and 41 will be explained later.

Further, an accelerator pedal 42 has a load sensor 43 connected to it which generates an output voltage which is proportional to the amount of depression of the accelerator pedal 42. The output voltage of the load sensor 43 is input to the input port 36 through a corresponding AD converter 38. The crank angle sensor 44 generates an output pulse every time, for example, a crankshaft rotates by 15 degrees. This output pulse is input to the input port 36. The CPU 35 calculates the engine speed from the output pulse of this crank angle sensor 44. On the other hand, the output port 37 is connected through corresponding drive circuits 45 to the spark plugs 10, fuel injectors 11, and throttle valve drive actuator 17. Note that the ECU 31 functions as control means for controlling the internal combustion engine based on the outputs of various sensors, etc.

<Configuration of Air-Fuel Ratio Sensor>

Figure 3:
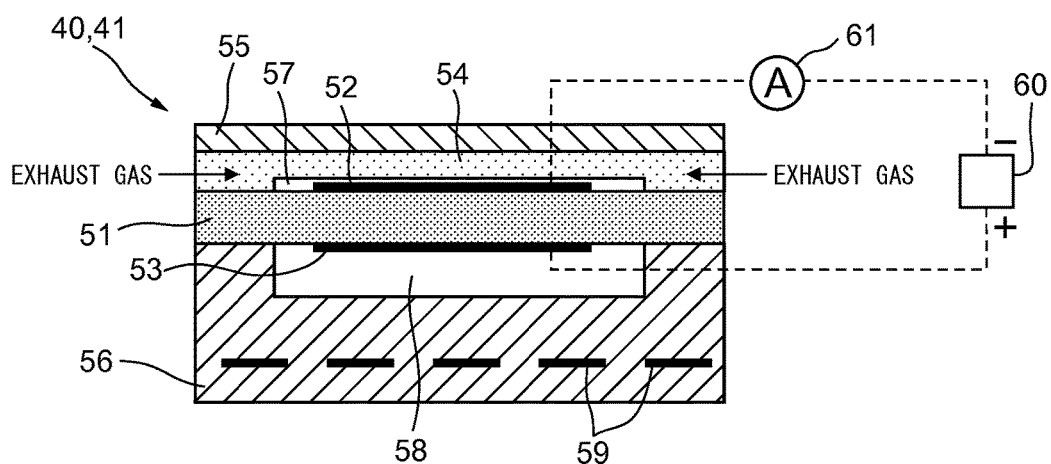
FIG. 3 is a schematic cross-sectional view of an air-fuel ratio sensor.

Next, referring to FIG. 3, the configurations of air-fuel ratio sensors 40 and 41 in the present embodiment will be explained. FIG. 3 is a schematic cross-sectional view of air-fuel ratio sensors 40 and 41. As will be understood from FIG. 3, the air-fuel ratio sensors 40 and 41 in the present embodiment are single-cell type air-fuel ratio sensors each comprised of a solid electrolyte layer and a pair of electrodes forming a single cell.

As shown in FIG. 3, each of the air-fuel ratio sensors 40 and 41 is provided with a solid electrolyte layer 51, an exhaust side electrode (first electrode) 52 which is arranged at one lateral surface of the solid electrolyte layer 51, an atmosphere side electrode (second electrode) 53 which is arranged at the other lateral surface of the solid electrolyte layer 51, a diffusion regulation layer 54 which regulates the diffusion of the passing exhaust gas, a protective layer 55 which protects the diffusion regulation layer 54, and a heater part 56 which heats the air-fuel ratio sensor 40 or 41.

On one lateral surface of the solid electrolyte layer 51, a diffusion regulation layer 54 is provided. On the lateral surface of the diffusion regulation layer 54 at the opposite side from the lateral surface of the solid electrolyte layer 51 side, a protective layer 55 is provided. In the present embodiment, a measured gas chamber 57 is formed between the solid electrolyte layer 51 and the diffusion regulation layer 54. In this measured gas chamber 57, the gas to be detected by the air-fuel ratio sensors 40 and 41, that is, the exhaust gas, is introduced through the diffusion regulation layer 54. Further, the exhaust side electrode 52 is arranged inside the measured gas chamber 57, therefore, the exhaust side electrode 52 is exposed to the exhaust gas through the diffusion regulation layer 54. Note that, the measured gas chamber 57 does not necessarily have to be provided. The diffusion regulation layer 54 may directly contact the surface of the exhaust side electrode 52.

On the other lateral surface of the solid electrolyte layer 51, the heater part 56 is provided. Between the solid electrolyte layer 51 and the heater part 56, a reference gas chamber 58 is formed. Inside this reference gas chamber 58, a reference gas is introduced. In the present embodiment, the reference gas chamber 58 is open to the atmosphere. Therefore, inside the reference gas chamber 58, the atmosphere is introduced as the reference gas. The atmosphere side electrode 53 is arranged inside the reference gas chamber 58, therefore, the atmosphere side electrode 53 is exposed to the reference gas (reference atmosphere).). In the present embodiment, atmospheric air is used as the reference gas, so the atmosphere side electrode 53 is exposed to the atmosphere.

The heater part 56 is provided with a plurality of heaters 59. These heaters 59 can be used to control the temperature of the air-fuel ratio sensor 40 or 41, in particular, the temperature of the solid electrolyte layers 51. The heater part 56 has a sufficient heat generation capacity for heating the solid electrolyte layer 51 until activating.

The solid electrolyte layer 51 is formed by a sintered body of $ZrO_2$ (zirconia), $HfO_2$, $ThO_2$, $Bi_2O_3$, or other oxygen ion conducting oxide in which CaO, MgO, $Y_2O_3$, $Yb_2O_3$, etc. is blended as a stabilizer. Further, the diffusion regulation layer 54 is formed by a porous sintered body of alumina, magnesia, silica, spinel, mullite, or another heat resistant inorganic substance. Furthermore, the exhaust side electrode 52 and atmosphere side electrode 53 is formed by platinum or other precious metal with a high catalytic activity.

Further, between the exhaust side electrode 52 and the atmosphere side electrode 53, sensor voltage Vr is supplied by the voltage supply device 60 which is mounted on the ECU 31. In addition, the ECU 31 is provided with a current detection device 61 which detects the current (output current) which flows between these electrodes 52 and 53 through the solid electrolyte layer 51 when the voltage supply device 60 supplies the sensor voltage Vr. The current which is detected by this current detection device 61 is the output current of the air-fuel ratio sensors 40 and 41.

<Operation of Air-Fuel Ratio Sensor>

Next, referring to FIG. 4, the basic concept of the operation of the thus configured air-fuel ratio sensors 40, 41 will be explained. FIG. 4 is a view which schematically shows the operation of the air-fuel ratio sensors 40, 41. At the time of use, each of the air-fuel ratio sensors 40, 41 is arranged so that the protection layer 55 and the outer circumferential surface of the diffusion regulating layer 54 are exposed to the exhaust gas. Further, atmospheric air is introduced into the reference gas chamber 58 of the air-fuel ratio sensors 40, 41.

In the above-mentioned way, the solid electrolyte layer 51 is formed by a sintered body of an oxygen ion conductive oxide. Therefore, it has the property of an electromotive force E being generated which makes oxygen ions move from the high concentration lateral surface side to the low concentration lateral surface side if a difference occurs in the oxygen concentration between the two lateral surfaces of the solid electrolyte layer 51 in the state activated by the high temperature (oxygen cell characteristic).

Conversely, if a potential difference occurs between the two lateral surfaces, the solid electrolyte layer 51 has the characteristic of trying to make the oxygen ions move so that a ratio of oxygen concentration occurs between the two lateral surfaces of the solid electrolyte layer in accordance with the potential difference (oxygen pump characteristic). Specifically, when a potential difference occurs across the two lateral surfaces, movement of oxygen ions is caused so that the oxygen concentration at the lateral surface which has a positive polarity becomes higher than the oxygen concentration at the lateral surface which has a negative polarity, by a ratio according to the potential difference. Further, as shown in FIGS. 3 and 4, in the air-fuel ratio sensors 40, 41, a constant sensor applied voltage Vr is applied across electrodes 52, 53 so that the atmosphere side electrode 53 becomes the positive electrode and the exhaust side electrode 52 becomes the negative electrode.

When the exhaust air-fuel ratio around the air-fuel ratio sensors 40, 41 is leaner than the stoichiometric air-fuel ratio, the ratio of the oxygen concentrations between the two lateral surfaces of the solid electrolyte layer 51 does not become that large. Therefore, if setting the sensor applied voltage Vr at a suitable value, between the two lateral surfaces of the solid electrolyte layer 51, the actual oxygen concentration ratio becomes smaller than the oxygen concentration ratio corresponding to the sensor applied voltage Vr. For this reason, the oxygen ions move from the exhaust side electrode 52 toward the atmosphere side electrode 43 as shown in FIG. 4(A) so that the oxygen concentration ratio between the two lateral surfaces of the solid electrolyte layer 51 becomes larger toward the oxygen concentration ratio corresponding to the sensor applied voltage Vr. As a result, current flows from the positive side of the voltage application device 60 which applies the sensor applied voltage Vr, through the atmosphere side electrode 53, solid electrolyte layer 51, and exhaust side electrode 52, to the negative side of the voltage application device 60.

The magnitude of the current (output current) Ir flowing at this time is proportional to the amount of oxygen flowing by diffusing from the exhaust through the diffusion regulating layer 54 to the measured gas chamber 57, if setting the sensor applied voltage Vr to a suitable value. Therefore, by detecting the magnitude of this current Ir by the current detection device 61, it is possible to learn the oxygen concentration and in turn possible to learn the air-fuel ratio in the lean region.

On the other hand, when the exhaust air-fuel ratio around the air-fuel ratio sensors 40, 41 is richer than the stoichiometric air-fuel ratio, unburned gas flows in from the exhaust through the diffusion regulating layer 54 to the inside of the measured gas chamber 57, and therefore even if there is oxygen present on the exhaust side electrode 52, oxygen reacts with the unburned gas and is removed. Therefore, inside the measured gas chamber 57, the oxygen concentration becomes extremely low. As a result, the ratio of the oxygen concentration between the two lateral surfaces of the solid electrolyte layer 51 becomes large. For this reason, if setting the sensor applied voltage Vr to a suitable value, between the two lateral surfaces of the solid electrolyte layer 51, the actual oxygen concentration ratio will become larger than the oxygen concentration ratio corresponding to the sensor applied voltage Vr. Therefore, as shown in FIG. 4(B), oxygen ions move from the atmosphere side electrode 53 toward the exhaust side electrode 52 so that the oxygen concentration ratio between the two lateral surfaces of the solid electrolyte layer 51 becomes smaller toward the oxygen concentration ratio corresponding to the sensor applied voltage Vr. As a result, current flows from the atmosphere side electrode 53, through the voltage application device 60 which applies the sensor applied voltage Vr, to the exhaust side electrode 52.

The magnitude of the current (output current) Ir flowing at this time is determined by the flow rate of oxygen ions which move through the solid electrolyte layer 51 from the atmosphere side electrode 53 to the exhaust side electrode 52, if setting the sensor applied voltage Vr to a suitable value. The oxygen ions react (burn) with the unburned gas, which diffuses from the exhaust through the diffusion regulating layer 54 to the measured gas chamber 57, on the exhaust side electrode 52. Accordingly, the flow rate in movement of the oxygen ions corresponds to the concentration of unburned gas in the exhaust gas flowing into the measured gas chamber 57. Therefore, by detecting the magnitude of this current Ir by the current detection device 61, it is possible to learn the concentration of unburned gas and in turn possible to learn the air-fuel ratio in the rich region.

Further, when the exhaust air-fuel ratio around the air-fuel ratio sensors 40, 41 is the stoichiometric air-fuel ratio, the amounts of oxygen and unburned gas which flow into the measured gas chamber 57 become a chemical equivalent ratio. Therefore, due to the catalytic action of the exhaust side electrode 52, oxygen and unburned gas completely burn and no fluctuation arises in the concentrations of oxygen and unburned gas in the measured gas chamber 57. As a result, the oxygen concentration ratio across the two lateral surfaces of the solid electrolyte layer 51 does not fluctuate, but is maintained at the oxygen concentration ratio corresponding to the sensor applied voltage Vr. For this reason, as shown in FIG. 4(C), no movement of oxygen ions occurs due to the oxygen pump characteristic. As a result, no current flows through the circuits.

<Circuits of Voltage Application Device and Current Detection Device>

Figure 5:
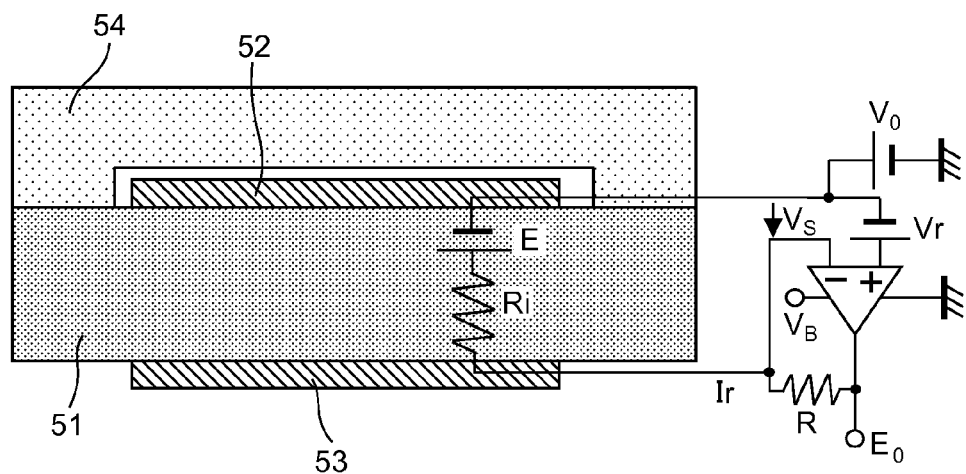
FIG. 5 is a view which shows an example of a specific circuit which forms a voltage application device and current detection device.

FIG. 5 shows an example of the specific circuits which form the voltage application device 60 and current detection device 61. In the illustrated example, the electromotive force E which occurs due to the oxygen cell characteristic is expressed as "E", the internal resistance of the solid electrolyte layer 51 is expressed as "Ri", and the difference of electrical potential across the two electrodes 52, 53 is expressed as "Vs".

As will be understood from FIG. 5, the voltage application device 60 basically performs negative feedback control so that the electromotive force E which occurs due to the oxygen cell characteristic matches the sensor applied voltage Vr. In other words, the voltage application device 60 performs negative feedback control so that even when a change in the oxygen concentration ratio between the two lateral surfaces of the solid electrode layer 51 causes the potential difference Vs between the two electrodes 52 and 53 to change, this potential difference Vs becomes the sensor applied voltage Vr.

Therefore, when the exhaust air-fuel ratio becomes the stoichiometric air-fuel ratio and no change occurs in the oxygen concentration ratio between the two lateral surfaces of the solid electrolyte layer 51, the oxygen concentration ratio between the two lateral surfaces of the solid electrolyte layer 51 becomes the oxygen concentration ratio corresponding to the sensor applied voltage Vr. In this case, the electromotive force E conforms to the sensor applied voltage Vr, the potential difference Vs between the two electrodes 52 and 53 also becomes the sensor applied voltage Vr, and, as a result, the current Ir does not flow.

On the other hand, when the exhaust air-fuel ratio becomes an air-fuel ratio which is different from the stoichiometric air-fuel ratio and a change occurs in the oxygen concentration ratio between the two lateral surfaces of the solid electrolyte layer 51, the oxygen concentration ratio between the two lateral surfaces of the solid electrolyte layer 51 does not become an oxygen concentration ratio corresponding to the sensor applied voltage Vr. In this case, the electromotive force E becomes a value different from the sensor applied voltage Vr. As a result, due to negative feedback control, a potential difference Vs is applied between the two electrodes 52 and 53 so that oxygen ions move between the two lateral surfaces of the solid electrolyte layer 51 so that the electromotive force E conforms to the sensor applied voltage Vr. Further, current Ir flows along with movement of oxygen ions at this time. As a result, the electromotive force E converges to the sensor applied voltage Vr. If the electromotive force E converges to the sensor applied voltage Vr, finally the potential difference Vs also converges to the sensor applied voltage Vr.

Therefore, the voltage application device 60 can be said to substantially apply the sensor applied voltage Vr between the two electrodes 52 and 53. Note that, the electrical circuit of the voltage application device 60 does not have to be one such as shown in FIG. 5. The circuit may be any form of device so long as able to substantially apply the sensor applied voltage Vr across the two electrodes 52, 53.

Further, the current detection device 61 does not actually detect the current. It detects the voltage $E_0$ to calculate the current from this voltage $E_0$. In this regard, $E_0$ is expressed as in the following equation (1).

$$E_0 = Vr + V_0 + I_r R \quad (1)$$

wherein, $V_0$ is the offset voltage (voltage applied so that $E_0$ does not become a negative value, for example, 3V), while R is the value of the resistance shown in FIG. 5.

In equation (1), the sensor applied voltage Vr, offset voltage $V_0$, and resistance value R are constant, and therefore the voltage $E_0$ changes in accordance with the current Ir. For this reason, if detecting the voltage $E_0$, it is possible to calculate the current Ir from that voltage $E_0$.

Therefore, the current detection device 61 can be said to substantially detect the current Ir which flows across the two electrodes 52, 53. Note that, the electrical circuit of the current detection device 61 does not have to be one such as shown in FIG. 5. If possible to detect the current Ir flowing across the two electrodes 52, 53, any form of device may be used.

<Output Characteristic of Air-Fuel Ratio Sensor>

Figure 6:
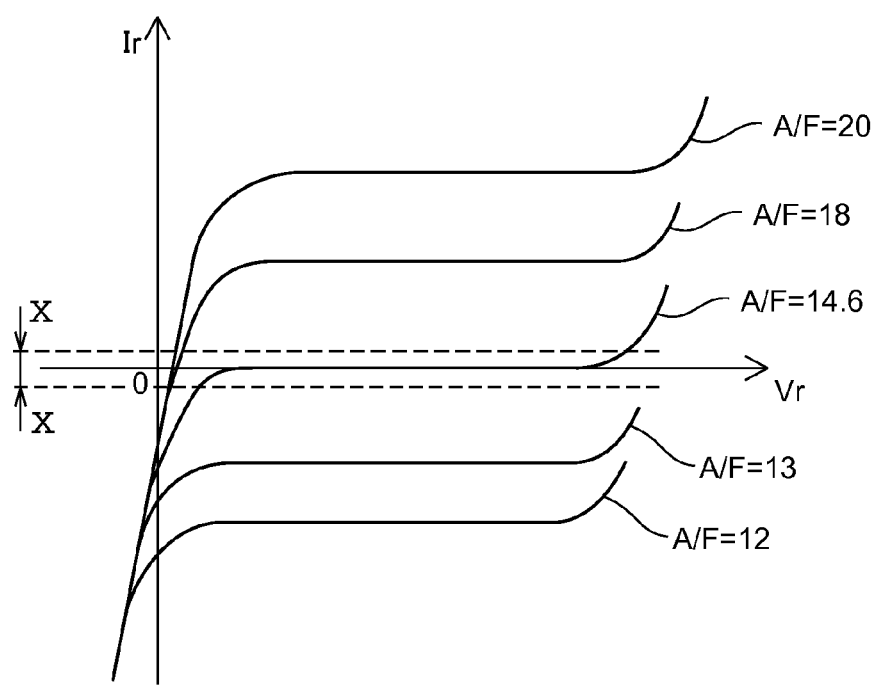
FIG. 6 is a view which shows the relationship between a sensor applied voltage and output current at different exhaust air-fuel ratios.

The air-fuel ratio sensors 40, 41 which are configured and operate as stated above, have the voltage-current (V-I) characteristic such as shown in FIG. 6. As will be understood from FIG. 6, in the region where the sensor applied voltage Vr is not more than 0 and near 0, when the exhaust air-fuel ratio is constant, if the sensor applied voltage Vr gradually increases from a negative value, the output current Ir increases along with this.

That is, in this voltage region, since the sensor applied voltage Vr is low, the flow rate of oxygen ions which can move through the solid electrolyte layer 51 is small. For this reason, the flow rate of oxygen ions which can move through the solid electrolyte layer 51 becomes smaller than the rate of inflow of exhaust gas through the diffusion regulating layer 54 and, accordingly, the output current Ir changes in accordance with the flow rate of oxygen ions which can move through the solid electrolyte layer 51. The flow rate of oxygen ions which can move through the solid electrolyte layer 51 changes in accordance with the sensor applied voltage Vr, and, as a result, the output current increases along with the increase in the sensor applied voltage Vr. Note that, the voltage region where the output current Ir changes in proportion to the sensor applied voltage Vr in this way is called the "proportional region". Further, when the sensor applied voltage Vr is 0, the output current Ir becomes a negative value since an electromotive force E according to the oxygen concentration ratio is generated between the two lateral surfaces of the solid electrolyte layer 51, by the oxygen cell characteristic.

Then, if leaving the exhaust air-fuel ratio constant and gradually increasing the sensor applied voltage Vr, the ratio of increase of output current to the increase of the voltage will gradually become smaller and will finally substantially be saturated. As a result, even if increasing the sensor applied voltage Vr, the output current will no longer change much at all. This substantially saturated current is called the "limit current". Below, the voltage region where this limit current occurs will be called the "limit current region".

That is, in this limit current region, the sensor applied voltage Vr is high to a certain extent, and therefore the flow rate of oxygen ions which can move through the solid electrolyte layer 51 is large. Therefore, the flow rate of oxygen ions which can move through the solid electrolyte layer 51 becomes greater than the rate of inflow of exhaust gas through the diffusion regulating layer 54. Therefore, the output current Ir changes in accordance with the concentration of oxygen or concentration of unburned gas in the exhaust gas flowing into the measured gas chamber 57 through the diffusion regulating layer 54. Even if making the exhaust air-fuel ratio constant and changing the sensor applied voltage Vr, basically, the concentration of oxygen or concentration of unburned gas in the exhaust gas flowing into the measured gas chamber 57 through the diffusion regulating layer 54 does not change, and therefore the output voltage Ir does not change.

However, if the exhaust air-fuel ratio differs, the concentration of oxygen and concentration of unburned gas in the exhaust gas flowing into the measured gas chamber 57 through the diffusion regulating layer 54 also differ, and therefore the output current Ir changes in accordance with the exhaust air-fuel ratio. As will be understood from FIG. 6, between the lean air-fuel ratio and the rich air-fuel ratio (the air-furl ratio richer than the stoichiometric air-fuel ratio), the direction of flow of the limit current is opposite. At the time of the lean air-fuel ratio, the absolute value of the limit current becomes larger the larger the air-fuel ratio, while at the time of the rich air-fuel ratio, the absolute value of the limit current becomes larger the smaller the air-fuel ratio.

Then, if holding the exhaust air-fuel ratio constant and further increasing the sensor applied voltage Vr, the output current Ir again starts to increase along with the increase in the voltage. If applying a high sensor applied voltage Vr in this way, the moisture which is contained in the exhaust gas breaks down on the exhaust side electrode 52. Along with this, current flows. Further, if further increasing the sensor applied voltage Vr, even with just breakdown of moisture, the current no longer becomes sufficient. At this time, the solid electrolyte layer 51 breaks down. Below, the voltage region where moisture and the solid electrolyte layer 51 break down in this way will be called the "moisture breakdown region".

Figure 7:
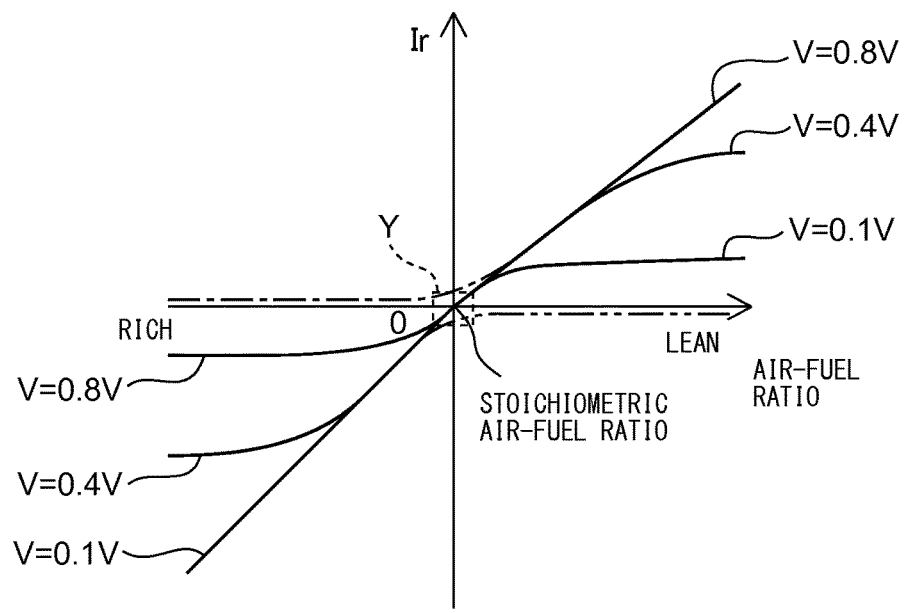
FIG. 7 is a view which shows the relationship between the exhaust air-fuel ratio and output current at different sensor applied voltages.

FIG. 7 is a view which shows the relationship between the exhaust air-fuel ratio and the output current Ir at different sensor applied voltages Vr. As will be understood from FIG. 7, if the sensor applied voltage Vr is 0.1V to 0.9V or so, the output current Ir changes in accordance with the exhaust air-fuel ratio at least near the stoichiometric air-fuel ratio. Further, as will be understood from FIG. 7, if sensor applied voltage Vr is 0.1V to 0.9V or so, near the stoichiometric air-fuel ratio, the relationship between the exhaust air-fuel ratio and the output current Ir is substantially the same regardless of the sensor applied voltage Vr.

On the other hand, as will be understood from FIG. 7, if the exhaust air-fuel ratio becomes lower than a certain exhaust air-fuel ratio or less, the output current Ir no longer changes much at all even if the exhaust air-fuel ratio changes. This certain exhaust air-fuel ratio changes in accordance with the sensor applied voltage Vr. It becomes higher the higher the sensor applied voltage Vr. For this reason, if making the sensor applied voltage Vr increase to a certain specific value or more, as shown in the figure by the one-dot chain line, no matter what the value of the exhaust air-fuel ratio, the output current Ir will no longer become 0.

On the other hand, if the exhaust air-fuel ratio becomes higher than a certain exhaust air-fuel ratio or more, the output current Ir no longer changes much at all even if the exhaust air-fuel ratio changes. This certain exhaust air-fuel ratio also changes in accordance with the sensor applied voltage Vr. It becomes lower the lower the sensor applied voltage Vr. For this reason, if making the sensor applied voltage Vr decrease to a certain specific value or less, as shown in the figure by the two-dot chain line, no matter what the value of the exhaust air-fuel ratio, the output current Ir will no longer become 0 (for example, when the sensor applied voltage Vr is set to 0V, the output current Ir does not become 0 regardless of the exhaust air-fuel ratio).

<Microscopic Characteristics Near Stoichiometric Air-Fuel Ratio>

The inventors of the present invention engaged in in-depth research whereupon they discovered that if viewing the relationship between the sensor applied voltage Vr and the output current Ir (FIG. 6) or the relationship between the exhaust air-fuel ratio and output current Ir (FIG. 7) macroscopically, they trend like explained above, but if viewing these relationships microscopically near the stoichiometric air-fuel ratio, they trend differently from the above. Below, this will be explained.

Figure 8:
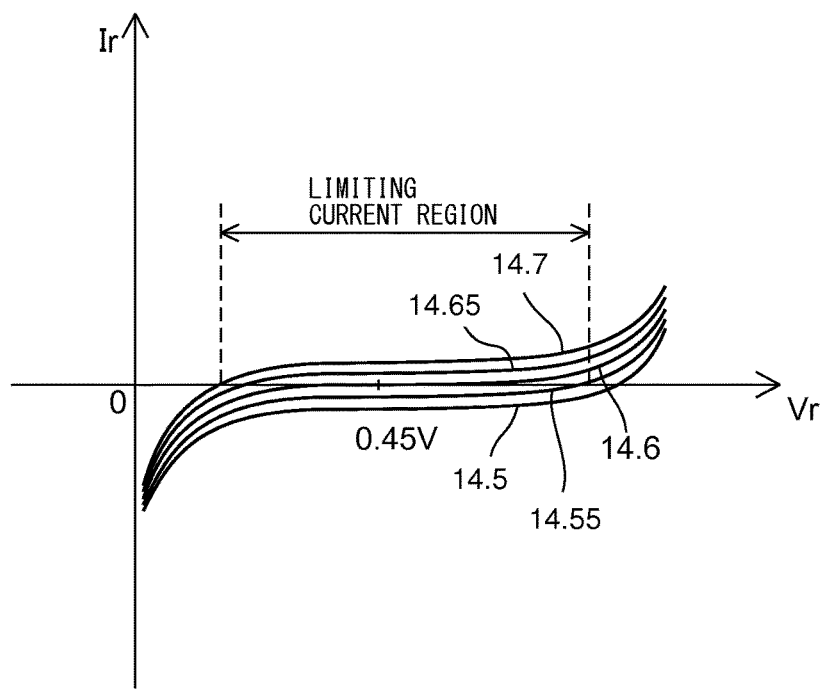
FIG. 8 is a view which shows enlarged the region which is shown by X-X in FIG. 6.

FIG. 8 is a view which shows enlarged the region where the output current Ir becomes near 0 (region shown by X-X in FIG. 6), regarding the voltage-current graph of FIG. 6. As will be understood from FIG. 8, even in the limit current region, when making the exhaust air-fuel ratio constant, the output current Ir also increases, though very slightly, along with the increase in the sensor applied voltage Vr. For example, considering the case where the exhaust air-fuel ratio is the stoichiometric air-fuel ratio (14.6) as an example, when the sensor applied voltage Vr is 0.45V or so, the output current Ir becomes 0. As opposed to this, if setting the sensor applied voltage Vr lower than 0.45V by a certain extent (for example, 0.2V), the output current becomes a value lower than 0. On the other hand, if setting the sensor applied voltage Vr higher than 0.45V by a certain extent (for example, 0.7V), the output current becomes a value higher than 0.

Figure 9:
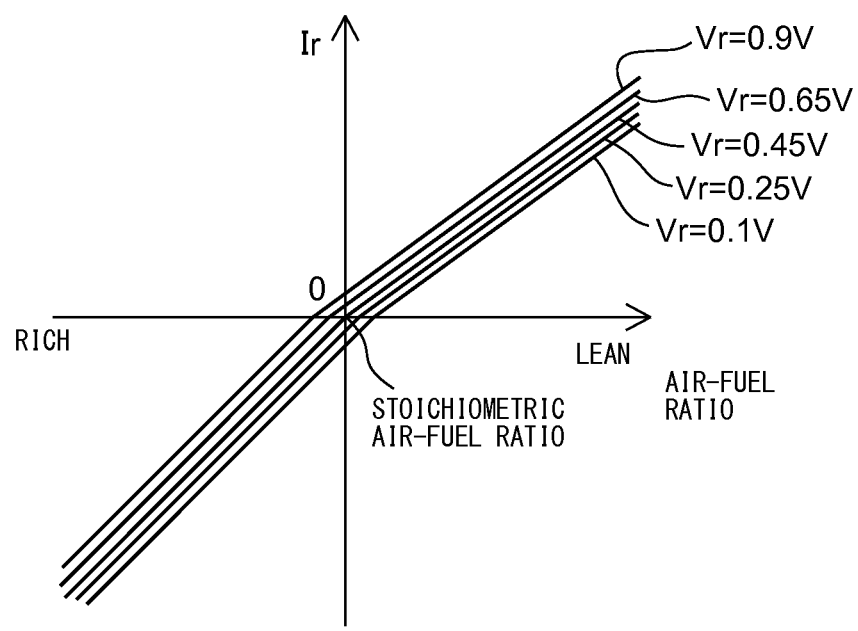
FIG. 9 is a view which shows enlarged the region which is shown by Y in FIG. 7.

FIG. 9 is a view which shows enlarged the region where the exhaust air-fuel ratio is near the stoichiometric air-fuel ratio and the output current Ir is near 0 (region shown by Y in FIG. 7), regarding the air-fuel ratio-current graph of FIG. 7. From FIG. 9, it will be understood that in the region near the stoichiometric air-fuel ratio, the output current Ir for the same exhaust air-fuel ratio slightly differs for each sensor applied voltage Vr. For example, in the illustrated example, when the exhaust air-fuel ratio is the stoichiometric air-fuel ratio, the output current Ir when the sensor applied voltage Vr is 0.45V becomes 0. Further, if setting the sensor applied voltage Vr larger than 0.45V, the output current Ir also becomes larger than 0. If making the sensor applied voltage Vr smaller than 0.45V, the output current Ir also becomes smaller than 0.

In addition, from FIG. 9, it will be understood that the exhaust air-fuel ratio when the output current Ir is 0 (below, referred to as "exhaust air-fuel ratio at the time of zero current") differs for each sensor applied voltage Vr. In the illustrated example, when the sensor applied voltage Vr is 0.45V, the output current Ir becomes 0 when the exhaust air-fuel ratio is the stoichiometric air-fuel ratio. As opposed to this, if the sensor applied voltage Vr is larger than 0.45V, the output current Ir becomes 0 when the exhaust air-fuel ratio is richer than the stoichiometric air-fuel ratio. The larger the sensor applied voltage Vr becomes, the smaller the exhaust air-fuel ratio at the time of zero current. Conversely, if the sensor applied voltage Vr is smaller than 0.45V, the output current Ir becomes 0 when the exhaust air-fuel ratio is leaner than the stoichiometric air-fuel ratio. The smaller the sensor applied voltage Vr, the larger the exhaust air-fuel ratio at the time of zero current. That is, by making the sensor applied voltage Vr change, it is possible to change the exhaust air-fuel ratio at the time of zero current.

Figure 2:
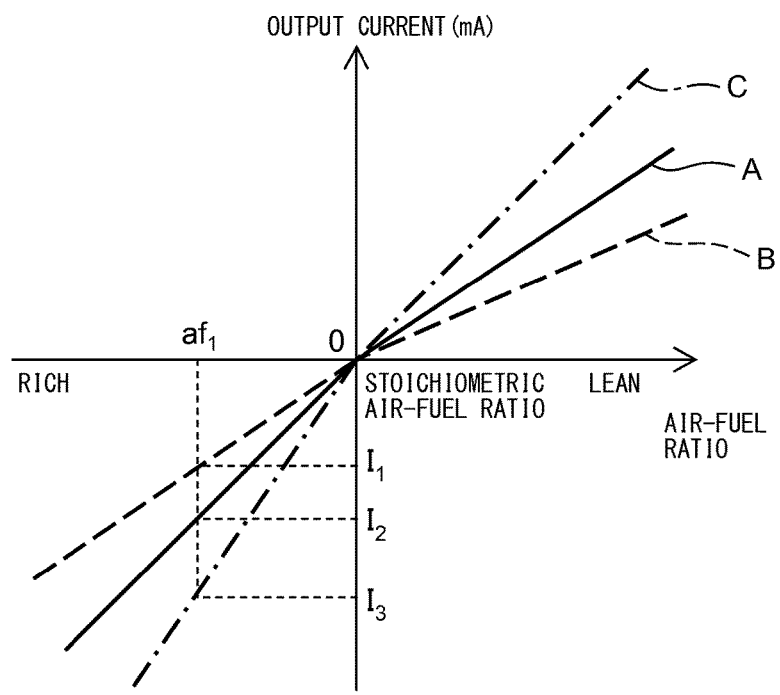
FIG. 2 is a view which shows an output characteristic of an air-fuel ratio sensor.

In this regard, as explained using FIG. 2, the rate of change of output current varies between individual air-fuel ratio sensors. Even with the same air-fuel ratio sensor, variation occurs along with aging, etc. However, as will be understood from FIG. 2, even if such variation occurs, the exhaust air-fuel ratio at the time of zero current (in the example of FIG. 2, the stoichiometric air-fuel ratio) does not change much at all. That is, when the output current Ir is a value other than zero, it is difficult to accurately detect the absolute value of the exhaust air-fuel ratio, while when the output current Ir becomes zero, it is possible to accurately detect the absolute value of the exhaust air-fuel ratio (in the example of FIG. 2, the stoichiometric air-fuel ratio).

Further, as explained using FIG. 9, in the air-fuel ratio sensors 40, 41, by changing the sensor applied voltage Vr, it is possible to change the exhaust air-fuel ratio at the time of zero current. That is, if suitably setting the sensor applied voltage Vr, it is possible to accurately detect the absolute value of an exhaust air-fuel ratio other than the stoichiometric air-fuel ratio. In particular, when changing the sensor applied voltage Vr within a later explained "specific voltage region", it is possible to adjust the exhaust air-fuel ratio at the time of zero current only slightly with respect to the stoichiometric air-fuel ratio (14.6) (for example, within a range of ±1% (about 14.45 to about 14.75)). Therefore, by suitably setting the sensor applied voltage Vr, it becomes possible to accurately detect the absolute value of an air-fuel ratio which slightly differs from the stoichiometric air-fuel ratio.

<Explanation of Specific Voltage Region>

As explained above, by changing the sensor applied voltage Vr, it is possible to change the exhaust air-fuel ratio at the time of zero current. However, if changing the sensor applied voltage Vr so as to be larger than a certain upper limit voltage or smaller than a certain lower limit voltage, the amount of change in the exhaust air-fuel ratio at the time of zero current, with respect to the amount of change in the sensor applied voltage Vr, becomes larger. Therefore, in these voltage regions, if the sensor applied voltage Vr slightly shifts, the exhaust air-fuel ratio at the time of zero current greatly changes. Therefore, in this voltage region, to accurately detect the absolute value of the exhaust air-fuel ratio, it becomes necessary to precisely control the sensor applied voltage Vr. This is not that practical. Therefore, from the viewpoint of accurately detecting the absolute value of the exhaust air-fuel ratio, the sensor applied voltage Vr has to be a value within a "specific voltage region" between a certain upper limit voltage and a certain lower limit voltage.

This specific voltage region can be defined by various methods. Below, FIG. 10 to FIG. 12 will be used to explain an example of several definitions.

First, a first example will be explained. As shown by the voltage-current graph of FIG. 10(A), the air-fuel ratio sensors 40, 41 have a current increase region which is a voltage region where the output current Ir increases along with an increase of the sensor applied voltage Vr for each exhaust air-fuel ratio, and a current fine increase region which is a voltage region where the amount of increase of the output current Ir with respect the amount of increase of the sensor applied voltage Vr becomes smaller than that in the current increase region, due to the provision of the diffusion regulating layer (in FIG. 10(A), current increase region and current fine increase region are shown only for when the exhaust air-fuel ratio is the stoichiometric air-fuel ratio). In a first example, the current fine increase region of when the exhaust air-fuel ratio is the stoichiometric air-fuel ratio is defined as the "specific voltage region".

Next, a second example will be explained. As shown by the voltage-current graph of FIG. 10(B), the air-fuel ratio sensors 40, 41 have a limit current region which is a voltage region where the output current Ir becomes a limit current for each exhaust air-fuel ratio (in FIG. 10(B), limit current region is shown only for when the exhaust air-fuel ratio is the stoichiometric air-fuel ratio). In a second example, the limit current region when the exhaust air-fuel ratio is the stoichiometric air-fuel ratio is defined as the "specific voltage region".

Next, a third example will be explained. As shown by the voltage-current graph of FIG. 10(C), the air-fuel ratio sensors 40, 41 have a proportional region which is a voltage region where the output current increases in proportion to an increase in the applied voltage for each exhaust air-fuel ratio, a moisture breakdown region which is a voltage region where the output current changes in accordance with a change in the applied voltage due to breakdown of water and the solid electrolyte layer 51, and an intermediate region which is a voltage region between these proportional region and moisture breakdown region (in FIG. 10(C), proportional region, moisture breakdown region, and intermediate region shown only for when the exhaust air-fuel ratio is the stoichiometric air-fuel ratio). In a third example, the intermediate region where the exhaust air-fuel ratio is the stoichiometric air-fuel ratio is defined as a "specific voltage region".

Figure 11:
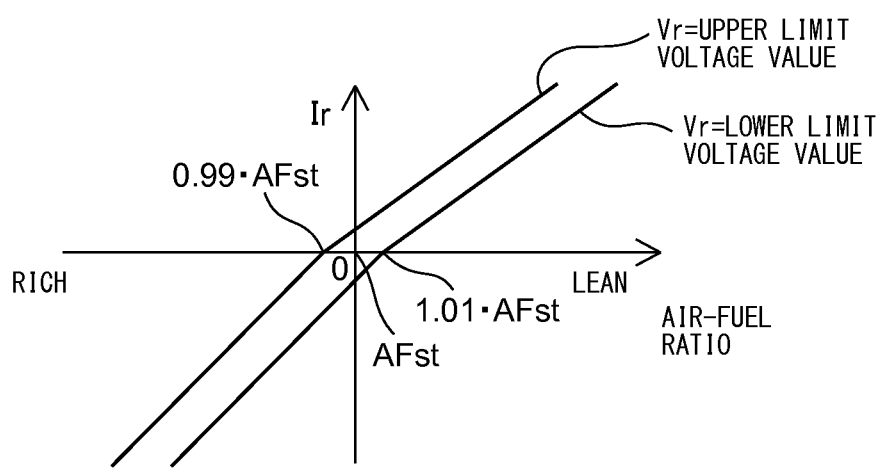
FIG. 11 is a view which shows the relationship between the air-fuel ratio of the air-fuel ratio sensor and the output current.

Next, a fourth example will be explained. As shown in FIG. 9, the exhaust air-fuel ratio at the time of zero current changes in accordance with the sensor applied voltage Vr. The higher the sensor applied voltage Vr, the lower the exhaust air-fuel ratio at the time of zero current. As shown in FIG. 11, in the air-fuel ratio sensors 40, 41 in the present embodiment, when the sensor applied voltage Vr is set to the upper limit voltage value, the exhaust air-fuel ratio at the time of zero current becomes an air-fuel ratio which is for example 0.5 to 2% or so (preferably 1% or so) lower than the stoichiometric air-fuel ratio AFst. On the other hand, when the sensor applied voltage Vr is set to the lower limit voltage value, the exhaust air-fuel ratio at the time of zero current becomes an air-fuel ratio which is for example 0.5 to 2% or so (preferably 1% or so) higher than the stoichiometric air-fuel ratio AFst. In a fourth example, the voltage region between the upper limit voltage value (voltage value where exhaust air-fuel ratio at the time of zero current becomes an air-fuel ratio lower by for example 1% from the stoichiometric air-fuel ratio AFst) and the lower limit voltage value (voltage value where exhaust air-fuel ratio at the time of zero current becomes an air-fuel ratio higher by for example 1% from the stoichiometric air-fuel ratio AFst) is defined as the "specific voltage region".

Figure 12:
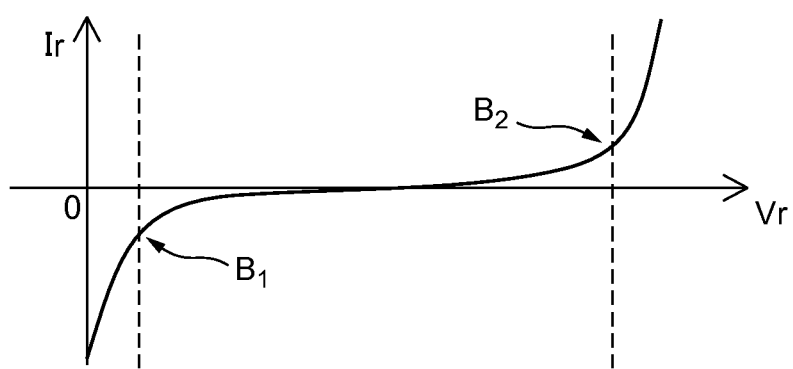
FIG. 12 is a view which shows the relationship between the sensor applied voltage and the output current.

Next, referring to FIG. 12, a fifth example will be explained. FIG. 12 shows a change in current with respect to the voltage. As shown in FIG. 12, in the air-fuel ratio sensors 40, 41 of the present embodiment, at each exhaust air-fuel ratio, the output current Ir increases until the first curved point $B_1$ as the sensor applied voltage Vr increases from the negative state, the output current Ir increases until the second curved point $B_2$ as the sensor applied voltage Vr increases from the first curved point $B_1$, and the output current Ir increases as the sensor applied voltage Vr increases from the second curved point. In the voltage region between the first curved point $B_1$ and second curved point $B_2$, the amount of increase of the output current Ir with respect to the amount of increase of the sensor applied voltage Vr is smaller than in the other voltage regions. In the fifth example, the voltage region between the first curved point and second curved point when the first exhaust air-fuel ratio is the stoichiometric air-fuel ratio is defined as the "specific voltage region".

Next, a sixth example will be explained. In the sixth example, the upper limit voltage value and the lower limit voltage value of the "specific voltage region" are specified by specific numerical values. Specifically, the "specific voltage region" is 0.05V to 0.95V, preferably 0.1V to 0.9V, more preferably 0.15V to 0.8V.

Note that, as explained using FIG. 7, if increasing the sensor applied voltage Vr to a certain specific value (maximum voltage) or more, as shown in the figure by the one-dot chain line, no matter what value the exhaust air-fuel ratio is, the output current Ir will no longer become 0. On the other hand, if decreasing the sensor applied voltage Vr to a certain specific value (minimum voltage) or less, as shown in the figure by the two-dot chain line, no matter what value the exhaust air-fuel ratio, the output current Ir will no longer become 0.

Therefore, if the sensor applied voltage Vr is a voltage between the maximum voltage and the minimum voltage, there is an exhaust air-fuel ratio where the output current becomes zero. Conversely, if the sensor applied voltage Vr is a voltage higher than the maximum voltage or a voltage lower than the minimum voltage, there is no exhaust air-fuel ratio where the output current will become zero. Therefore, the sensor applied voltage Vr at least has to be able to be a voltage where the output current becomes zero when the exhaust air-fuel ratio is any air-fuel ratio, that is, a voltage between the maximum voltage and the minimum voltage. The above-mentioned "specific voltage region" is the voltage region between the maximum voltage and the minimum voltage.

<Applied Voltage at Individual Air-Fuel Ratio Sensors>

In the present embodiment, considering the above-mentioned microscopic characteristics, when detecting the air-fuel ratio of the exhaust gas by the upstream side air-fuel ratio sensor 40, the sensor applied voltage Vrup at the upstream side air-fuel ratio sensor 40 is fixed to a constant voltage (for example, 0.4V to 0.45V) where the output current becomes zero when the exhaust air-fuel ratio is the stoichiometric air-fuel ratio (in the present embodiment, 14.6). In other words, in the upstream side air-fuel ratio sensor 40, the sensor applied voltage Vrup is set so that the exhaust air-fuel ratio at the time of zero current becomes the stoichiometric air-fuel ratio.

On the other hand, when detecting the air-fuel ratio of the exhaust gas by the downstream side air-fuel ratio sensor 41, the sensor applied voltage Vr at the downstream side air-fuel ratio sensor 41 is fixed to a voltage (for example, 0.2V) where the output current becomes zero when the exhaust air-fuel ratio is a predetermined air-fuel ratio slightly leaner than the stoichiometric air-fuel ratio (for example, 14.65. Below, referred to as "lean judged air-fuel ratio"). In other words, in the downstream side air-fuel ratio sensor 41, the sensor applied voltage Vrdwn is set so that exhaust air-fuel ratio at the time of zero current becomes a lean judged air-fuel ratio which is slightly leaner than the stoichiometric air-fuel ratio (below, also referred to as the "rich judged applied voltage Vrrich").

Therefore, the sensor applied voltage Vr at the downstream side air-fuel ratio sensor 41 is set to a voltage which is lower than the voltage by which the output current becomes zero when the exhaust air-fuel ratio is the stoichiometric air-fuel ratio. Further, voltage in which the output current becomes zero when the exhaust air-fuel ratio is the stoichiometric air-fuel ratio is 0.45V or so, and therefore the sensor applied voltage Vr at the downstream side air-fuel ratio sensor 41 is set to a voltage which is lower than 0.45V.

Whatever the case, in the present embodiment, the sensor applied voltage Vrdwn at the downstream side air-fuel ratio sensor 41 is set to a voltage which is lower than the sensor applied voltage Vrup at the upstream side air-fuel ratio sensor 40.

Therefore, the ECU 31 which is connected to the two air-fuel ratio sensors 40, 41 judges that the exhaust air-fuel ratio around the upstream side air-fuel ratio sensor 40 is the stoichiometric air-fuel ratio, when the output current Irup of the upstream side air-fuel ratio sensor 40 is zero. On the other hand, the ECU 31 judges that the exhaust air-fuel ratio around the downstream side air-fuel ratio sensor 41 is the lean judged air-fuel ratio, that is, a predetermined air-fuel ratio which is leaner than the stoichiometric air-fuel ratio, when the output current Irdwn of the downstream side air-fuel ratio sensor 41 is zero.

Note that, as the time when the air-fuel ratio sensor detects the air-fuel ratio of the exhaust gas, for example, when not performing the later explained fuel cut control, or when the air-fuel ratio detected by the air-fuel ratio sensor is not a high value of 18 or more, etc., may be mentioned.

<Explanation of Exhaust Purification Catalyst>

Next, the exhaust purification catalysts 20, 24 which are used in the present embodiment will be explained. The upstream side exhaust purification catalyst 20 and the downstream side exhaust purification catalyst 24 both have similar configurations. Below, only the upstream side exhaust purification catalyst 20 will be explained, but the downstream side exhaust purification catalyst 24 may also have a similar configuration and action.

The upstream side exhaust purification catalyst 20 is a three-way catalyst which has an oxygen storage ability. Specifically, the upstream side exhaust purification catalyst 20 is comprised of a carrier made of ceramic on which a precious metal which has a catalytic action (for example, platinum (Pt)) and a substance which has an oxygen storage ability (for example, ceria ($CeO_2$)) are carried. If the upstream side exhaust purification catalyst 20 reaches a predetermined activation temperature, it exhibits an oxygen storage ability in addition to the catalytic action of simultaneously removing the unburned gas (HC, CO, etc.) and nitrogen oxides ($NO_X$).

According to the oxygen storage ability of the upstream side exhaust purification catalyst 20, the upstream side exhaust purification catalyst 20 stores the oxygen in the exhaust gas, when the air-fuel ratio of the exhaust gas flowing into the upstream side exhaust purification catalyst 20 is leaner than the stoichiometric air-fuel ratio (lean air-fuel ratio). On the other hand, the upstream side exhaust purification catalyst 20 releases the oxygen which is stored in the upstream side exhaust purification catalyst 20 when the air-fuel ratio of the inflowing exhaust gas is richer than the stoichiometric air-fuel ratio (rich air-fuel ratio). Note that, the "air-fuel ratio of the exhaust gas" means the ratio of the mass of the fuel to the mass of the air which are fed up to when the exhaust gas is produced. Usually, it means the ratio of the mass of the fuel to the mass of the air which are fed into the combustion chamber 5 when that exhaust gas is produced.

The upstream side exhaust purification catalyst 20 has a catalytic action and an oxygen storage ability, and therefore has the action of removing $NO_X$ and unburned gas in accordance with the oxygen storage amount. FIG. 13 shows the relationship between the oxygen storage amount of the upstream side exhaust purification catalyst 20 and the concentration of $NO_X$ and unburned gas (HC, CO, etc.) which flow out from the upstream side exhaust purification catalyst 20. FIG. 13(A) shows the relationship between the oxygen storage amount and the concentration of $NO_X$ in the exhaust gas flowing out from the upstream side exhaust purification catalyst 20, when the air-fuel ratio of the exhaust gas flowing into the upstream side exhaust purification catalyst 20 is a lean air-fuel ratio. On the other hand, FIG. 13(B) shows the relationship between the oxygen storage amount and the concentration of unburned gas in the exhaust gas flowing out from the upstream side exhaust purification catalyst 20, when the air-fuel ratio of the exhaust gas flowing into the upstream side exhaust purification catalyst 20 is a rich air-fuel ratio.

As will be understood from FIG. 13(A), when the oxygen storage amount of the upstream side exhaust purification catalyst 20 is small, there is an extra margin up to the maximum oxygen storage amount. For this reason, even if the air-fuel ratio of the exhaust gas flowing into the upstream side exhaust purification catalyst 20 is a lean air-fuel ratio (that is, this exhaust gas includes $NO_X$ and oxygen), the oxygen in the exhaust gas is stored in the exhaust purification catalyst. Along with this, $NO_X$ is also reduced and purified. As a result, the exhaust gas flowing out from the upstream side exhaust purification catalyst 20 does not contain almost any $NO_X$.

However, if the oxygen storage amount of the upstream side exhaust purification catalyst 20 increases, when the air-fuel ratio of the exhaust gas flowing into the upstream side exhaust purification catalyst 20 is a lean air-fuel ratio, it becomes difficult for the upstream side exhaust purification catalyst 20 to store the oxygen in the exhaust gas. Along with this, the $NO_X$ in the exhaust gas also becomes harder to be reduced and purified. For this reason, as will be understood from FIG. 13(A), if the oxygen storage amount increases over a certain upper limit storage amount Cuplim, the concentration of $NO_X$ in the exhaust gas flowing out from the upstream side exhaust purification catalyst 20 rapidly rises.

On the other hand, when the oxygen storage amount of the upstream side exhaust purification catalyst 20 is large, if the air-fuel ratio of the exhaust gas flowing into the upstream side exhaust purification catalyst 20 is the rich air-fuel ratio (that is, this exhaust gas contains unburned gas), oxygen stored in the upstream side exhaust purification catalyst 20 is released. For this reason, the unburned gas in the exhaust gas flowing into the upstream side exhaust purification catalyst 20 is oxidized and purified. As a result, as will be understood from FIG. 13(B), the exhaust gas flowing out from the upstream side exhaust purification catalyst 20 does not contain almost any unburned gas.

However, if the oxygen storage amount of the upstream side exhaust purification catalyst 20 becomes smaller, when the air-fuel ratio of the exhaust gas flowing into the upstream side exhaust purification catalyst 20 is the rich air-fuel ratio, the oxygen released from the upstream side exhaust purification catalyst 20 becomes smaller. Along with this, the unburned gas in the exhaust gas flowing into the upstream side exhaust purification catalyst 20 also becomes harder to be oxidized and purified. For this reason, as will be understood from FIG. 13(B), if the oxygen storage amount decreases beyond a certain lower limit storage amount Clowlim, the concentration of unburned gas in the exhaust gas flowing out from the upstream side exhaust purification catalyst 20 rapidly rises.

In this way, according to the exhaust purification catalysts 20, 24 used in the present embodiment, the characteristic of purification of $NO_X$ and unburned gas in the exhaust gas changes in accordance with the air-fuel ratio of the exhaust gas flowing into the exhaust purification catalysts 20, 24 and oxygen storage amount. Note that, as long as the exhaust purification catalysts 20, 24 has a catalytic function and oxygen storage ability, the exhaust purification catalysts 20, 24 may also be catalysts which are different from three-way catalysts.

<Summary of Control of Air-Fuel Ratio>

Next, a summary of the air-fuel ratio control in a control system of an internal combustion engine of the present invention will be explained. In the present embodiment, based on the output current Irup of the upstream side air-fuel ratio sensor 40, feedback control is performed so that the output current (that is, the air-fuel ratio of the exhaust gas flowing into the upstream side exhaust purification catalyst 20) Irup of the upstream side air-fuel ratio sensor 40 becomes a value corresponding to the target air-fuel ratio.

The target air-fuel ratio of the exhaust gas flowing into the upstream side exhaust purification catalyst 20 is set based on the output current Irdwn of the downstream side air-fuel ratio sensor 41. Specifically, the target air-fuel ratio is set to the lean set air-fuel ratio when the output current Irdwn of the downstream side air-fuel ratio sensor 41 becomes rich judged reference value Irefri or less, and is maintained at that air-fuel ratio. The fact that the output current Irdwn becomes the rich judged reference value Irefri or less means that the air-fuel ratio of the exhaust gas flowing out from the upstream side exhaust purification catalyst 20 becomes a predetermined rich judged air-fuel ratio (for example, 14.55), which is slightly richer than the stoichiometric air-fuel ratio, or less. Further, the lean set air-fuel ratio is a predetermined air-fuel ratio leaner than the stoichiometric air-fuel ratio by a certain extent. For example, it is 14.65 to 20, preferably 14.68 to 18, more preferably 14.7 to 16 or so.

If the target air-fuel ratio is changed to the lean set air-fuel ratio, the oxygen storage amount OSAsc of the upstream side exhaust purification catalyst 20 is estimated. The oxygen storage amount OSAsc is estimated based on the output current Irup of the upstream side air-fuel ratio sensor 40, and the estimated value of the amount of intake air to the combustion chamber 5, which is calculated based on the air flow meter 39, etc., or the amount of fuel injection from the fuel injector 11, etc. Further, if the estimated value of the oxygen storage amount OSAsc becomes a predetermined judged reference storage amount Cref or more, the target air-fuel ratio which was the lean set air-fuel ratio up to then is changed to a weak rich set air-fuel ratio and is maintained at that air-fuel ratio. The weak rich set air-fuel ratio is a predetermined air-fuel ratio slightly richer than the stoichiometric air-fuel ratio. For example, it is 13.5 to 14.58, preferably 14 to 14.57, more preferably 14.3 to 14.55 or so. After that, when the output current Irdwn of the downstream side air-fuel ratio sensor 41 again becomes rich judged reference value Irefri or less, the target air-fuel ratio is again set to the lean set air-fuel ratio, and then a similar operation is repeated.

In this way, in the present embodiment, the target air-fuel ratio of the exhaust gas flowing into the upstream side exhaust purification catalyst 20 is alternately set to the lean set air-fuel ratio and the weak rich set air-fuel ratio. In particular, in the present embodiment, the difference between the lean set air-fuel ratio and the stoichiometric air-fuel ratio is larger than the difference between the weak rich set air-fuel ratio and the stoichiometric air-fuel ratio. Therefore, in the present embodiment, the target air-fuel ratio is alternately set to lean set air-fuel ratio for a short period of time and weak rich set air-fuel ratio for a long period of time.

<Explanation of Normal Control Using Time Chart>

Figure 14:
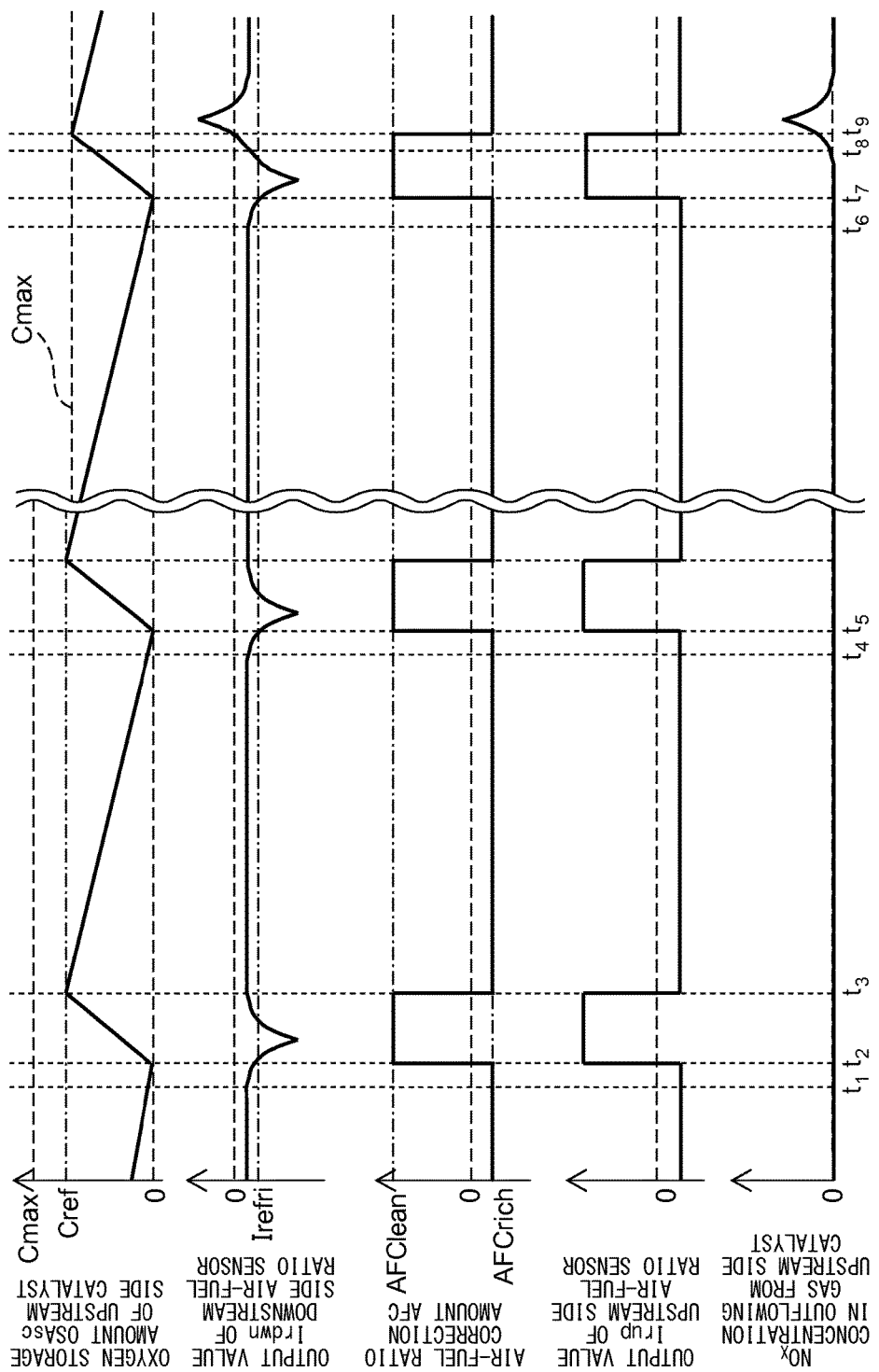
FIG. 14 is a time chart of the oxygen storage amount of the upstream side exhaust purification catalyst, etc.

Referring to FIG. 14, the above-mentioned such operation will be explained in detail. FIG. 14 is a time chart of the oxygen storage amount OSAsc of the upstream side exhaust purification catalyst 20, the output current Irdwn of the downstream side air-fuel ratio sensor 41, the air-fuel ratio shift amount AFC, the output current Irup of the upstream side air-fuel ratio sensor 40, and concentration of NOx in the exhaust gas flowing out from the upstream side exhaust purification catalyst 20 in the case of performing air-fuel ratio control in a control system of an internal combustion engine of the present invention.

Note that, as explained above, the output current Irup of the upstream side air-fuel ratio sensor 40 becomes zero when the air-fuel ratio of the exhaust gas flowing into the upstream side exhaust purification catalyst 20 is the stoichiometric air-fuel ratio, becomes a negative value when the air-fuel ratio of the exhaust gas is a rich air-fuel ratio, and becomes a positive value when the air-fuel ratio of the exhaust gas is a lean air-fuel ratio. Further, when the air-fuel ratio of the exhaust gas flowing into the upstream side exhaust purification catalyst 20 is a rich air-fuel ratio or lean air-fuel ratio, the greater the difference from the stoichiometric air-fuel ratio, the larger the absolute value of the output current Irup of the upstream side air-fuel ratio sensor 40.

On the other hand, the output current Irdwn of the downstream side air-fuel ratio sensor 41 becomes zero when the air-fuel ratio of the exhaust gas flowing out from the upstream side exhaust purification catalyst 20 is the lean judged air-fuel ratio (slightly leaner than stoichiometric air-fuel ratio), becomes a negative value when the air-fuel ratio of the exhaust gas is richer than the lean judged air-fuel ratio, and becomes a positive value when the air-fuel ratio of the exhaust gas is leaner than the lean judged air-fuel ratio. Further, when the air-fuel ratio of the exhaust gas flowing out from the upstream side exhaust purification catalyst 20 is leaner than the lean judged air-fuel ratio, the larger the difference from the lean judged air-fuel ratio, the larger the absolute value of the output current Irdwn of the downstream side air-fuel ratio sensor 41.

Further, the air-fuel ratio shift amount AFC is a shift amount relating to the target air-fuel ratio. When the air-fuel ratio shift amount AFC is 0, the target air-fuel ratio is the stoichiometric air-fuel ratio, when the air-fuel ratio shift amount AFC is a positive value, the target air-fuel ratio becomes a lean air-fuel ratio, and when the air-fuel ratio shift amount AFC is a negative value, the target air-fuel ratio becomes a rich air-fuel ratio.

In the illustrated example, in the state before the time $t_1$, the air-fuel ratio shift amount AFC is set to the weak rich set shift amount AFCrich. The weak rich set shift amount AFCrich is a value corresponding to the weak rich set air-fuel ratio and a value smaller than 0. Therefore, the target air-fuel ratio is set to a rich air-fuel ratio. Along with this, the output current Irup of the upstream side air-fuel ratio sensor 40 becomes a negative value. The exhaust gas flowing into the upstream side exhaust purification catalyst 20 contains unburned gas, and therefore the oxygen storage amount OSAsc of the upstream side exhaust purification catalyst 20 gradually decreases. However, the unburned gas contained in the exhaust gas is purified at the upstream side exhaust purification catalyst 20, and therefore the air-fuel ratio of the exhaust gas flowing out from the upstream side exhaust purification catalyst 20 becomes substantially the stoichiometric air-fuel ratio. For this reason, the output current Irdwn of the downstream side air-fuel ratio sensor becomes a negative value (corresponding to stoichiometric air-fuel ratio). At this time, the air-fuel ratio of the exhaust gas flowing into the upstream side exhaust purification catalyst 20 becomes a rich air-fuel ratio, and therefore the amount of $NO_X$ exhausted from the upstream side exhaust purification catalyst 20 is suppressed.

If the oxygen storage amount OSAsc of the upstream side exhaust purification catalyst 20 gradually decreases, the oxygen storage amount OSAsc decreases to less than the lower limit storage amount (see Clowlim of FIG. 13) at the time $t_1$. If the oxygen storage amount OSAsc decreases to less than the lower limit storage amount, part of the unburned gas flowing into the upstream side exhaust purification catalyst 20 flows out without being purified at the upstream side exhaust purification catalyst 20. For this reason, after the time $t_1$, the output current Irdwn of the downstream side air-fuel ratio sensor 41 gradually falls along with the decrease in the oxygen storage amount OSAsc of the upstream side exhaust purification catalyst 20. At this time as well, the air-fuel ratio of the exhaust gas flowing into the upstream side exhaust purification catalyst 20 becomes a rich air-fuel ratio, and therefore the amount of $NO_X$ exhausted from the upstream side exhaust purification catalyst 20 is suppressed.

Then, at the time $t_2$, the output current Irdwn of the downstream side air-fuel ratio sensor 41 reaches the rich judged reference value Irefri corresponding to the rich judged air-fuel ratio. In the present embodiment, if the output current Irdwn of the downstream side air-fuel ratio sensor 41 reaches the rich judged reference value Irefri, the air-fuel ratio shift amount AFC is switched to the lean set shift amount AFClean so as to suppress the decrease of the oxygen storage amount OSAsc of the upstream side exhaust purification catalyst 20. The lean set shift amount AFClean is a value corresponding to the lean set air-fuel ratio and is a value larger than 0. Therefore, the target air-fuel ratio is set to a lean air-fuel ratio.

Note that, in the present embodiment, the air-fuel ratio shift amount AFC is switched after the output current Irdwn of the downstream side air-fuel ratio sensor 41 reaches the rich judged reference value Irefri, that is, after the air-fuel ratio of the exhaust gas flowing out from the upstream side exhaust purification catalyst 20 reaches the rich judged air-fuel ratio. This is because even if the oxygen storage amount of the upstream side exhaust purification catalyst 20 is sufficient, the air-fuel ratio of the exhaust gas flowing out from the upstream side exhaust purification catalyst 20 sometimes deviates slightly from the stoichiometric air-fuel ratio. That is, if it is judged that the oxygen storage amount has decreased to less than the lower limit storage amount when the output current Irdwn deviates slightly from the value corresponding to the stoichiometric air-fuel ratio, even if there is actually a sufficient oxygen storage amount, there is a possibility that it is judged that the oxygen storage amount decreases to lower than the lower limit storage amount. Therefore, in the present embodiment, it is judged the oxygen storage amount decreases lower than the lower limit storage amount, only when the air-fuel ratio of the exhaust gas flowing out from the upstream side exhaust purification catalyst 20 reaches the rich judged air-fuel ratio. Conversely speaking, the rich judged air-fuel ratio is set to an air-fuel ratio which the air-fuel ratio of the exhaust gas flowing out from the upstream side exhaust purification catalyst 20 does not reach much at all when the oxygen storage amount of the upstream side exhaust purification catalyst 20 is sufficient.

At the time $t_2$, if switching the target air-fuel ratio to the lean air-fuel ratio, the air-fuel ratio of the exhaust gas flowing into the upstream side exhaust purification catalyst 20 also changes from the rich air-fuel ratio to the lean air-fuel ratio (in actuality, a delay occurs from when switching the target air-fuel ratio to when the air-fuel ratio of the exhaust gas flowing into the upstream side exhaust purification catalyst 20 changes, but in the illustrated example, it is assumed for convenience that these change simultaneously).

At the time $t_2$, if the air-fuel ratio of the exhaust gas flowing into the upstream side exhaust purification catalyst 20 changes to the lean air-fuel ratio, the oxygen storage amount OSAsc of the upstream side exhaust purification catalyst 20 increases. Further, along with this, the air-fuel ratio of the exhaust gas flowing out from the upstream side exhaust purification catalyst 20 changes to the stoichiometric air-fuel ratio, and the output current Irdwn of the downstream side air-fuel ratio sensor 41 also converges to a negative value corresponding to the stoichiometric air-fuel ratio. Note that, in the illustrated example, right after switching the target air-fuel ratio, the output current Irdwn of the downstream side air-fuel ratio sensor 41 falls. This is because a delay occurs from when switching the target air-fuel ratio to when the exhaust gas reaches the downstream side air-fuel ratio sensor 41.

Although the air-fuel ratio of the exhaust gas flowing into the upstream side exhaust purification catalyst 20 is a lean air-fuel ratio at this time, the upstream side exhaust purification catalyst 20 has sufficient leeway in the oxygen storage ability, and therefore the oxygen in the inflowing exhaust gas is stored in the upstream side exhaust purification catalyst 20 and the $NO_X$ is reduced and purified. For this reason, the amount of $NO_X$ exhausted from the upstream side exhaust purification catalyst 20 is suppressed.

Then, if the oxygen storage amount OSAsc of the upstream side exhaust purification catalyst 20 increases, at the time $t_3$, the oxygen storage amount OSAsc reaches the judged reference storage amount Cref. In the present embodiment, if the oxygen storage amount OSAsc becomes the judged reference storage amount Cref, the air-fuel ratio shift amount AFC is switched to a weak rich set shift amount AFCrich (value smaller than 0) to stop the storage of oxygen in the upstream side exhaust purification catalyst 20. Therefore, the target air-fuel ratio is set to the rich air-fuel ratio.

However, as explained above, a delay occurs from when the target air-fuel ratio is switched to when the air-fuel ratio of the exhaust gas flowing into the upstream side exhaust purification catalyst 20 actually changes. For this reason, even if switching at the time $t_3$, after a certain extent of time passes from it, the air-fuel ratio of the exhaust gas flowing into the upstream side exhaust purification catalyst 20 changes from the lean air-fuel ratio to the rich air-fuel ratio from. Therefore, the oxygen storage amount OSAsc of the upstream side exhaust purification catalyst 20 increases until the air-fuel ratio of the exhaust gas flowing into the upstream side exhaust purification catalyst 20 changes to the rich air-fuel ratio.

However, the judged reference storage amount Cref is set sufficiently lower than the maximum oxygen storage amount Cmax or the upper limit storage amount (see Cuplim in FIG. 13), and therefore even at the time $t_3$, the oxygen storage amount OSAsc does not reach the maximum oxygen storage amount Cmax or the upper limit storage amount. Conversely speaking, the judged reference storage amount Cref is set to an amount sufficiently small so that the oxygen storage amount OSAsc does not reach the maximum oxygen storage amount Cmax or the upper limit storage amount even if a delay occurs from when switching the target air-fuel ratio to when the air-fuel ratio of the exhaust gas flowing into the upstream side exhaust purification catalyst 20 actually changes. For example, the judged reference storage amount Cref is set to ¾ or less of the maximum oxygen storage amount Cmax, preferably ½ or less, more preferably ⅕ or less. Therefore, during times $t_2$ to $t_3$ as well, the amount of $NO_X$ exhausted from the upstream side exhaust purification catalyst 20 is suppressed.

After the time $t_3$, the air-fuel ratio shift amount AFC is set to the weak rich set shift amount AFCrich. Therefore, the target air-fuel ratio is set to the rich air-fuel ratio. Along with this, the output current Irup of the upstream side air-fuel ratio sensor 40 becomes a negative value. The exhaust gas flowing into the upstream side exhaust purification catalyst 20 contains unburned gas, and therefore the oxygen storage amount OSAsc of the upstream side exhaust purification catalyst 20 gradually decreases. At the time $t_4$, in the same way as the time $t_1$, the oxygen storage amount OSAsc decreases below the lower limit storage amount. At this time as well, the air-fuel ratio of the exhaust gas flowing into the upstream side exhaust purification catalyst 20 becomes a rich air-fuel ratio, and therefore the amount of $NO_X$ exhausted from the upstream side exhaust purification catalyst 20 is suppressed.

Next, at the time $t_5$, in the same way as the time $t_2$, the output current Irdwn of the downstream side air-fuel ratio sensor 41 reaches the rich judged reference value Irefri. Due to this, the air-fuel ratio shift amount AFC is switched to the value AFClean corresponding to the lean set air-fuel ratio. Then, the cycle of the above-mentioned times $t_1$ to $t_5$ is repeated.

As will be understood from the above explanation, according to the above embodiment, it is possible to constantly suppress the amount of $NO_X$ exhausted from the upstream side exhaust purification catalyst 20. That is, so long as performing the above-mentioned control, basically the amount of $NO_X$ exhausted from the upstream side exhaust purification catalyst 20 can be made smaller. Further, in the present embodiment, it is substantially sufficient to estimate the oxygen storage amount OSAsc for only the times $t_2$ to $t_3$. For this reason, compared with the case where it is necessary to estimate the oxygen storage amount over a long period of time, error occurs less easily in the estimated value of the oxygen storage amount. From this viewpoint as well, it is possible to suppress the amount of $NO_X$ exhausted from the upstream side exhaust purification catalyst 20. In addition, if the oxygen storage amount of the exhaust purification catalyst is maintained constant, the oxygen storage ability of the exhaust purification catalyst falls. As opposed to this, according to the present embodiment, the oxygen storage amount OSAsc constantly fluctuates up and down, and therefore the oxygen storage ability is kept from falling.

Note that, in the above embodiment, during the times $t_2$ to $t_3$, the air-fuel ratio shift amount AFC is maintained at the lean set shift amount AFClean. However, in this time period, the air-fuel ratio shift amount AFC does not necessarily have to be maintained constant. It may be set to vary, such as gradually decreasing, or temporarily being the rich air-fuel ratio. In the same way, in this embodiment, during the times $t_3$ to $t_5$, the air-fuel ratio shift amount AFC is maintained at the weak rich set shift amount AFrich. However, in this time period, the air-fuel ratio shift amount AFC does not necessarily have to be maintained constant. It may be set to vary, such as gradually decreasing, or temporarily being the lean air-fuel ratio.

However, even in this case, the air-fuel ratio shift amount AFC during the times $t_2$ to $t_3$ is set so that the difference between the average value of the target air-fuel ratio in that period and the stoichiometric air-fuel ratio becomes larger than the difference between the average value of the target air-fuel ratio during the times $t_3$ to $t_5$ and the stoichiometric air-fuel ratio.

Further, in the above embodiment, the oxygen storage amount OSAsc of the upstream side exhaust purification catalyst 20 is estimated based on the output current Irup of the upstream side air-fuel ratio sensor 40 and the estimated value of the intake air amount to the combustion chamber 5, etc. However, the oxygen storage amount OSAsc may also be calculated based on other parameters in addition to these parameters, or may also be estimated based on parameters different from these parameters. Further, in the above embodiment, if the estimated value of the oxygen storage amount OSAsc becomes the judged reference storage amount Cref or more, the target air-fuel ratio is switched from the lean set air-fuel ratio to the weak rich set air-fuel ratio. However, the timing for switching the target air-fuel ratio from the lean set air-fuel ratio to the weak rich set air-fuel ratio may be determined based on other parameters, such as, for example, the engine operating time from when switching the target air-fuel ratio from the weak rich set air-fuel ratio to the lean set air-fuel ratio. However, in this case as well, while the oxygen storage amount OSAsc of the upstream side exhaust purification catalyst 20 is estimated to be smaller than the maximum oxygen storage amount, the target air-fuel ratio has to be switched from the lean set air-fuel ratio to the weak rich set air-fuel ratio.

Considering the above, in the present embodiment, the ECU 31 can be said to comprise an oxygen storage amount increasing means for continuously or intermittently setting a target air-fuel ratio of the exhaust gas flowing into the upstream side exhaust purification catalyst to a lean set air-fuel ratio until the oxygen storage amount OSAsc of the upstream side exhaust purification catalyst becomes the judged reference storage amount Cref, when the air-fuel ratio of the exhaust gas detected by the downstream side air-fuel ratio sensor 41 becomes a rich judged air-fuel ratio or less, and an oxygen storage amount decreasing means for continuously or intermittently setting a target air-fuel ratio of the exhaust gas flowing into the upstream side exhaust purification catalyst to a weak rich set air-fuel ratio so that the oxygen storage amount OSAsc decreases toward zero without reaching the maximum storage amount Cmax, when the oxygen storage amount OSAsc of the upstream side exhaust purification catalyst 20 becomes the judged reference storage amount Cref or more.

In the meantime, even if performing the above-mentioned air-fuel ratio control, sometimes exhaust gas containing $NO_X$ flows out from the upstream side exhaust purification catalyst 20. For example, when the upstream side exhaust purification catalyst 20 deteriorates and the maximum oxygen storage amount Cmax of the upstream side exhaust purification catalyst 20 decreases, the oxygen storage amount OSAsc of the upstream side exhaust purification catalyst 20 reaches the maximum oxygen storage amount Cmax before reaching the judged reference storage amount Cref. Further, for example, even if something causes the air-fuel ratio of the exhaust gas flowing into the upstream side exhaust purification catalyst 20 to temporarily become much leaner than the stoichiometric air-fuel ratio or causes the lean duration become longer, the oxygen storage amount OSAsc of the upstream side exhaust purification catalyst 20 sometimes reaches the maximum oxygen storage amount Cmax.

Therefore, in the present embodiment, when the oxygen storage amount OSAsc of the upstream side exhaust purification catalyst 20 reaches near the maximum oxygen storage amount Cmax and $NO_X$ and oxygen flow out from the upstream side exhaust purification catalyst 20, the target air-fuel ratio is switched to the weak rich set air-fuel ratio. Specifically, when the air-fuel ratio detected by the downstream side air-fuel ratio sensor 41 becomes a lean judged air-fuel ratio which is leaner than the stoichiometric air-fuel ratio or one more than that, the target air-fuel ratio is switched to the weak rich set air-fuel ratio.

The region at the right side from the wavy line at the center of FIG. 14 shows as an example the case where the upstream side exhaust purification catalyst 20 deteriorates and the maximum oxygen storage amount Cmax of the upstream side exhaust purification catalyst 20 decreases. At the time $t_6$, in the same way as the time $t_1$, the oxygen storage amount OSAsc decreases over the lower limit storage amount and part of the oxygen and $NO_X$ in the exhaust gas flowing into the upstream side exhaust purification catalyst 20 flows out from the upstream side exhaust purification catalyst 20. Then, at the time $t_7$, the output current Irdwn of the downstream side air-fuel ratio sensor 41 becomes the rich judged reference value Irefri or less, and therefore the air-fuel ratio shift amount AFC is switched to the lean set shift amount AFClean. Therefore, the target air-fuel ratio of the exhaust gas flowing into the upstream side exhaust purification catalyst 20 is set to the lean air-fuel ratio.

Then, if the oxygen storage amount OSAsc of the upstream side exhaust purification catalyst 20 increases, since the maximum oxygen storage amount Cmax has been decreased, the oxygen storage amount OSAsc increases over the upper limit storage amount (see FIG. 13, Cuplim) at the time $t_8$. If the oxygen storage amount OSAsc increases over the upper limit storage amount, part of the $NO_X$ and oxygen flowing into the upstream side exhaust purification catalyst 20 flows out from the upstream side exhaust purification catalyst 20 without being purified or stored. For this reason, after the time $t_8$, along with the increase in the oxygen storage amount OSAsc of the upstream side exhaust purification catalyst 20, the output current Irdwn of the downstream side air-fuel ratio sensor 41 gradually increases.

Then, at the time $t_9$, the output current Irdwn of the downstream side air-fuel ratio sensor 41 reaches zero, which corresponds to the lean judged air-fuel ratio. In the present embodiment, if the output current Irdwn of the downstream side air-fuel ratio sensor 41 becomes zero, to suppress the increase in the oxygen storage amount OSAsc of the upstream side exhaust purification catalyst 20, the air-fuel ratio shift amount AFC is switched to the weak rich set shift amount. Therefore, the target air-fuel ratio of the exhaust gas flowing into the upstream side exhaust purification catalyst 20 is set to the rich air-fuel ratio. Note that, in the present embodiment, if the output current Irdwn of the downstream side air-fuel ratio sensor 41 becomes zero, the air-fuel ratio shift amount AFC is set to the weak rich set shift amount, but it may be set to another value as well so long as able to make target air-fuel ratio the rich air-fuel ratio.

At the time $t_9$, if switching the target air-fuel ratio to the rich air-fuel ratio, the air-fuel ratio of the exhaust gas flowing into the upstream side exhaust purification catalyst 20 also changes from the lean air-fuel ratio to the rich air-fuel ratio. As a result, the oxygen storage amount OSAsc of the upstream side exhaust purification catalyst 20 changes. Further, along with this, the air-fuel ratio of the exhaust gas flowing out from the upstream side exhaust purification catalyst 20 changes to the stoichiometric air-fuel ratio, and the output current Irdwn of the downstream side air-fuel ratio sensor 41 also converges to a value which corresponds to the stoichiometric air-fuel ratio. Note that, in the illustrated example, right after switching the target air-fuel ratio, the output current Irdwn of the downstream side air-fuel ratio sensor 41 increases. This is because a delay occurs from when switching the target air-fuel ratio to when the exhaust gas reaches the downstream side air-fuel ratio sensor 41.

In this way, in the present embodiment, if the fact of the exhaust gas flowing out from the upstream side exhaust purification catalyst 20 containing oxygen, that is, the fact that $NO_X$ is contained, is detected by the downstream side air-fuel ratio sensor 41, the target air-fuel ratio is switched to the rich air-fuel ratio. Due to this, it is possible to keep the outflow of $NO_X$ from the upstream side exhaust purification catalyst 20 to a minimum.

Furthermore, in the present embodiment, as explained above, the downstream side air-fuel ratio sensor 41 can accurately detect the absolute value at the lean judged air-fuel ratio. As explained using FIG. 2, in a conventional air-fuel ratio sensor, it was difficult to accurately detect the absolute value for an air-fuel ratio other than the stoichiometric air-fuel ratio. For this reason, in a conventional air-fuel ratio sensor, if error occurs in the output current by aging or individual differences, etc., even if the actual air-fuel ratio of the exhaust gas flowing out from the upstream side exhaust purification catalyst 20 differs from the lean judged air-fuel ratio, the output current of the air-fuel ratio sensor will be a value which corresponds to the lean judged air-fuel ratio. As a result, the timing of switching of the air-fuel ratio shift amount AFC to the weak rich set shift amount AFCrich, along with outflow of oxygen and $NO_X$ from the upstream side exhaust purification catalyst 20, will become delayed, or such switching will be performed at a timing not requiring such switching. As opposed to this, in the present embodiment, the downstream side air-fuel ratio sensor 41 can accurately detect the absolute value at the lean judged air-fuel ratio. For this reason, it is possible to keep the timing of switching of the air-fuel ratio shift amount AFC to the weak rich set shift amount AFCrich from becoming delayed or such switching from being performed at a timing not requiring such switching.

<Explanation of Specific Control>

Figure 15:
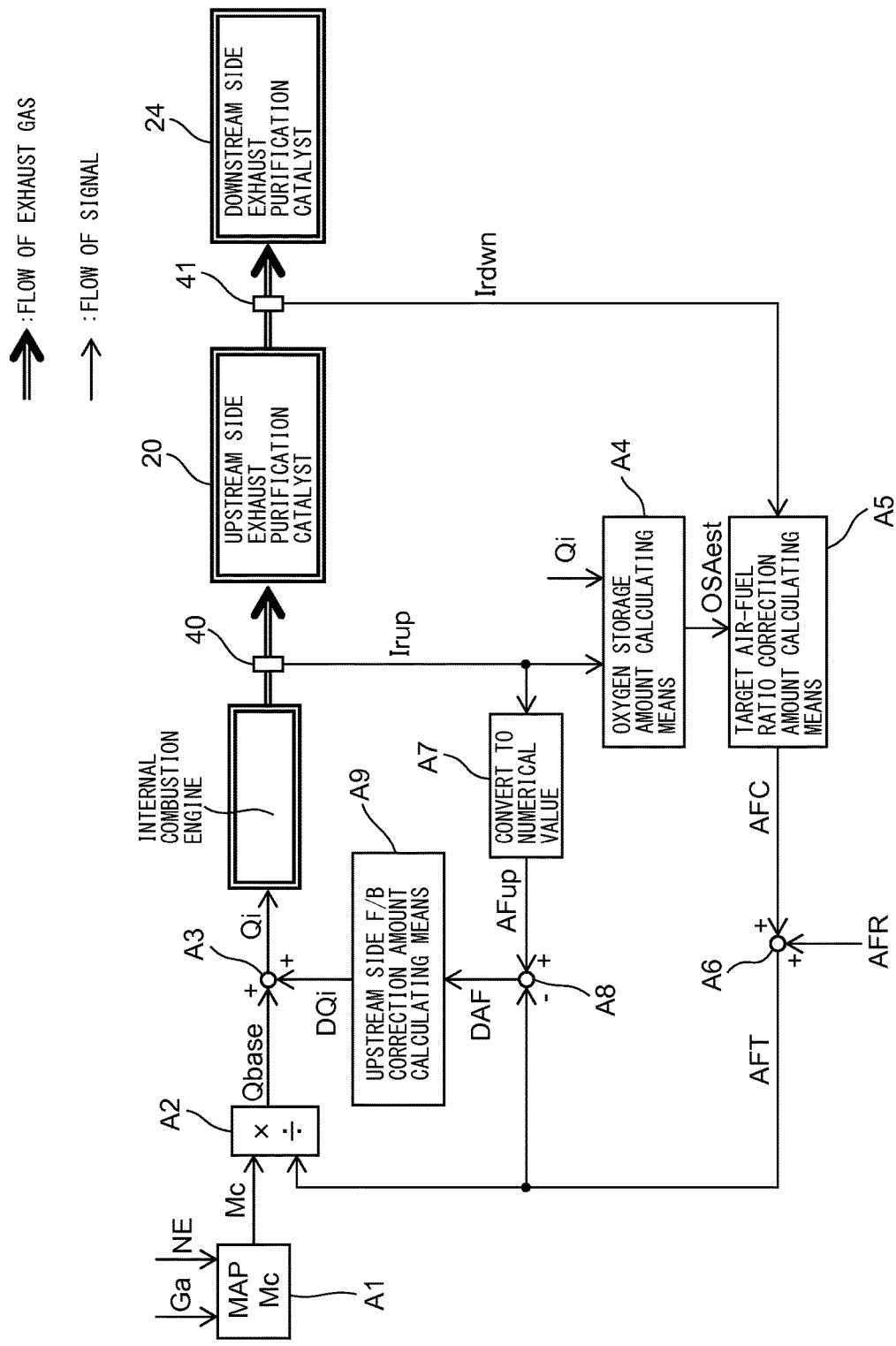
FIG. 15 is a functional block diagram of a control system.
Figure 16:
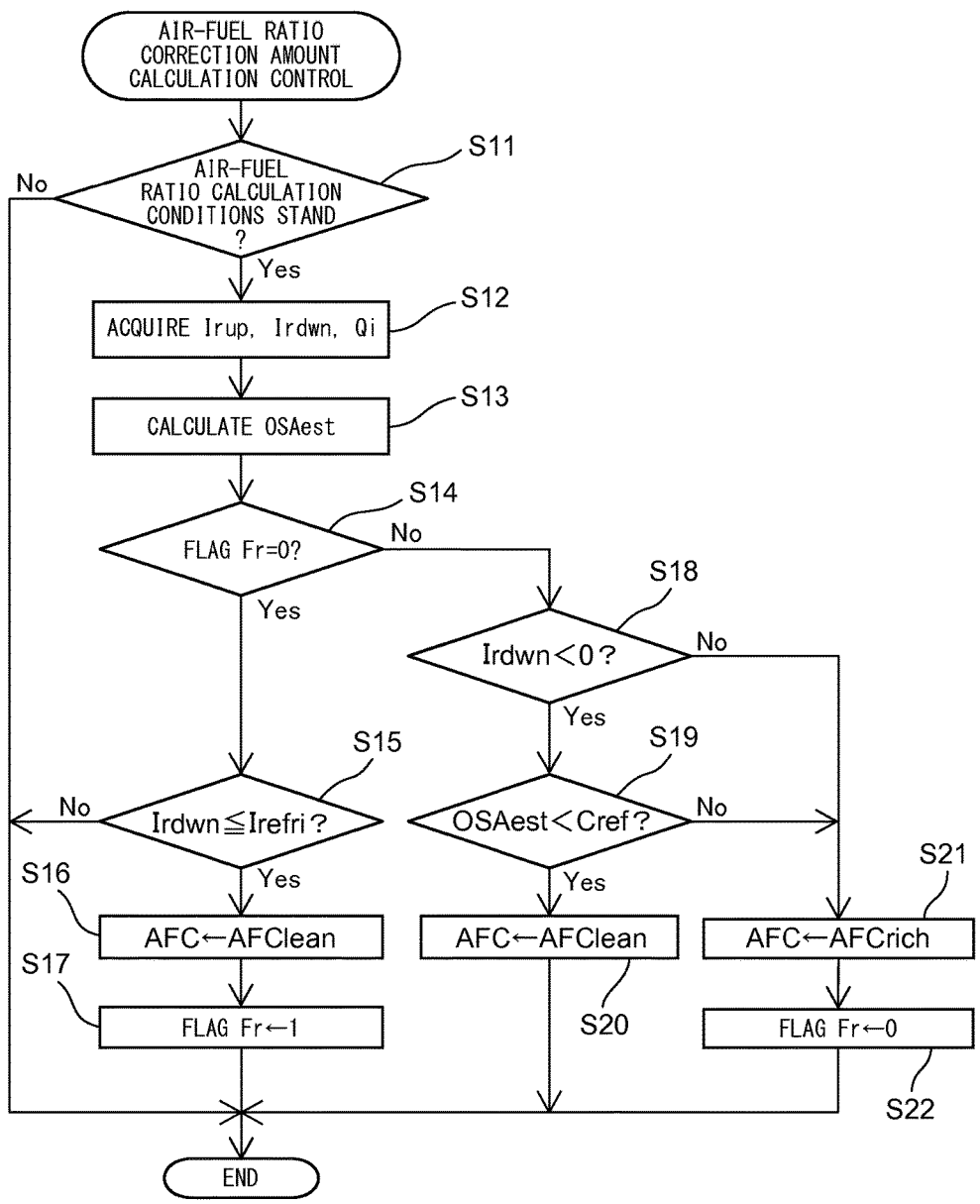
FIG. 16 is a flow chart which shows a control routine of control for calculation of an air-fuel ratio shift amount.

Next, referring to FIGS. 15 and 16, a control system in the above embodiment will be specifically explained. The control system in the present embodiment, as shown by the functional block diagram of FIG. 15, is configured including the functional blocks A1 to A9. Below, each functional block will be explained while referring to FIG. 15.

<Calculation of Fuel Injection>

First, calculation of the fuel injection will be explained. In calculating the fuel injection, the cylinder intake air calculating means A1, basic fuel injection calculating means A2, and fuel injection calculating means A3 are used.

The cylinder intake air calculating means A1 calculates the intake air amount Mc to each cylinder based on the intake air flow rate Ga measured by the air flow meter 39, the engine speed NE calculated based on the output of the crank angle sensor 44, and the map or calculation formula stored in the ROM 34 of the ECU 31.

The basic fuel injection calculating means A2 divides the cylinder intake air amount Mc, which is calculated by the cylinder intake air calculating means A1, by the target air-fuel ratio AFT which is calculated by the later explained target air-fuel ratio setting means A6 to thereby calculate the basic fuel injection amount Qbase (Qbase=Mc/AFT).

The fuel injection calculating means A3 adds the basic fuel injection amount Qbase calculated by the basic fuel injection calculating means A2 and the later explained F/B correction amount DQi, to calculate the fuel injection amount Qi (Qi=Qbase+DQi). The fuel injector 11 is commanded to inject fuel so that the fuel of the fuel injection amount Qi which was calculated in this way is injected.

<Calculation of Target Air-Fuel Ratio>

Next, calculation of the target air-fuel ratio will be explained. In calculation of the target air-fuel ratio, an oxygen storage amount calculating means A4, target air-fuel ratio shift amount calculating means A5, and target air-fuel ratio setting means A6 are used.

The oxygen storage amount calculating means A4 calculates the estimated value OSAest of the oxygen storage amount of the upstream side exhaust purification catalyst 20, based on the fuel injection amount Qi calculated by the fuel injection calculating means A3 and the output current Irup of the upstream side air-fuel ratio sensor 40. For example, the oxygen storage amount calculating means A4 multiplies the difference between the air-fuel ratio corresponding to the output current Irup of the upstream side air-fuel ratio sensor 40 and the stoichiometric air-fuel ratio, with the fuel injection amount Qi, and cumulatively adds the calculated values to calculate the estimated value OSAest of the oxygen storage amount. Note that, the oxygen storage amount calculating means A4 need not constantly estimate the oxygen storage amount of the upstream side exhaust purification catalyst 20. For example, it is possible to estimate the oxygen storage amount only for the period from when the target air-fuel ratio is actually switched from the rich air-fuel ratio to the lean air-fuel ratio (time $t_2$ in FIG. 14) to when the estimated value OSAest of the oxygen storage amount reaches the judged reference storage amount Cref (time $t_3$ in FIG. 14).

In the target air-fuel ratio shift amount calculating means A5, the air-fuel ratio shift amount AFC of the target air-fuel ratio is calculated, based on the estimated value OSAest of the oxygen storage amount calculated by the oxygen storage amount calculating means A4 and the output current Irdwn of the downstream side air-fuel ratio sensor 41. Specifically, the air-fuel ratio shift amount AFC is set to the lean set shift amount AFClean, when the output current Irdwn of the downstream side air-fuel ratio sensor 41 becomes the rich judged reference value or less. Then, the estimated value OSAest of the oxygen storage amount reaches the judged reference storage amount Cref, the air-fuel ratio shift amount AFC is set to the weak rich set shift amount AFCrich. After that, the air-fuel ratio shift amount AFC is maintained at a weak rich set shift amount AFCrich until the output current Irdwn of the downstream side air-fuel ratio sensor 41 becomes rich judged reference value Irefri or less. In addition, in the present embodiment, if the output current Irdwn of the downstream side air-fuel ratio sensor 41 becomes zero or more, the air-fuel ratio shift amount AFC is set to the weak rich set shift amount AFCrich.

The target air-fuel ratio setting means A6 adds the reference air-fuel ratio, which is, in the present embodiment, the stoichiometric air-fuel ratio AFR, and the air-fuel ratio shift amount AFC calculated by the target air-fuel ratio shift amount calculating means A5 to thereby calculate the target air-fuel ratio AFT. Therefore, the target air-fuel ratio AFT is set to either a weak rich set air-fuel ratio which is slightly richer than the stoichiometric air-fuel ratio AFR (when the air-fuel ratio shift amount AFC is a weak rich set shift amount AFCrich) or a lean set air-fuel ratio which is leaner by a certain extent than the stoichiometric air-fuel ratio AFR (when the air-fuel ratio shift amount AFC is a lean set shift amount AFClean). The thus calculated target air-fuel ratio AFT is input to the basic fuel injection calculating means A2 and the later explained air-fuel ratio difference calculating means A8.

FIG. 16 is a flow chart which shows a control routine of control for calculation of the air-fuel ratio shift amount AFC. The illustrated control routine is performed by interruption every certain time interval.

As shown in FIG. 16, first, at step S11, it is judged if the conditions for calculation of the air-fuel ratio shift amount AFC stand. As the case where the conditions for calculation of air-fuel ratio shift amount stand, for example, fuel cut control not being performed, etc., may be mentioned. If it is judged at step S11 that the conditions for calculation of the target air-fuel ratio stand, the routine proceeds to step S12. At step S12, the output current Irup of the upstream side air-fuel ratio sensor 40, the output current Irdwn of the downstream side air-fuel ratio sensor 41, and the fuel injection amount Qi are acquired. Next, at step S13, the estimated value OSAest of the oxygen storage amount is calculated based on the output current Irup of the upstream side air-fuel ratio sensor 40 and the fuel injection amount Qi, which were acquired at step S12.

Next, at step S14, it is judged if the lean set flag Fr is set to 0. The lean set flag Fr is set to "1" if the air-fuel ratio shift amount AFC is set to the lean set shift amount AFClean, and is set to "0" otherwise. If at step S14 the lean set flag Fr is set to "0", the routine proceeds to step S15. At step S15, it is judged if the output current Irdwn of the downstream side air-fuel ratio sensor 41 is the rich judged reference value Irefri or less. If it is judged that the output current Irdwn of the downstream side air-fuel ratio sensor 41 is larger than the rich judged reference value Irefri, the control routine is ended.

On the other hand, if the oxygen storage amount OSAsc of the upstream side exhaust purification catalyst 20 decreases and the air-fuel ratio of the exhaust gas flowing out from the upstream side exhaust purification catalyst 20 falls, at step S15, it is judged that the output current Irdwn of the downstream side air-fuel ratio sensor 41 is the rich judged reference value Irefri or less. In this case, the routine proceeds to step S16 where the air-fuel ratio shift amount AFC is set to the lean set shift amount AFClean. Next, at step S17, the lean set flag Fr is set to "1", and the control routine is ended.

At the next control routine, at step S14, it is judged that the lean set flag Fr is not set to "0" and the routine proceeds to step S18. At step S18, it is judged if the output current Irdwn of the downstream side air-fuel ratio sensor 41 is smaller than zero. If it is judged that the output current Irdwn of the downstream side air-fuel ratio sensor 41 is smaller than zero, the routine proceeds to step S19. At step S19, it is judged if the estimated value OSAest of the oxygen storage amount which is calculated at step S13 is smaller than the judged reference storage amount Cref. If it is judged that the estimated value OSAest of the oxygen storage amount is smaller than the judged reference storage amount Cref, the routine proceeds to step S20 where the air-fuel ratio shift amount AFC continues to be set to the lean set shift amount AFClean.

On the other hand, if the oxygen storage amount of the upstream side exhaust purification catalyst 20 increases, finally, at step S19, it is judged that the estimated value OSAest of the oxygen storage amount is the judged reference storage amount Cref or more, and then the routine proceeds to step S21. Further, if the oxygen storage amount of the upstream side exhaust purification catalyst 20 reaches near the maximum oxygen storage amount and $NO_X$ and oxygen flow out from the upstream side exhaust purification catalyst 20, at step S18, it is judged that the output current Irdwn of the downstream side air-fuel ratio sensor 41 is zero or more, and then the routine proceeds to step S21. At step S21, the air-fuel ratio shift amount AFC is set to the weak rich set shift amount AFCrich, next, at step S22, the lean set flag Fr is reset to "0", and the control routine is ended.

<Calculation of F/B Correction Amount>

Returning again to FIG. 15, calculation of the F/B correction amount based on the output current Irup of the upstream side air-fuel ratio sensor 40 will be explained. In calculation of the F/B correction amount, the numerical value converting means A7, air-fuel ratio difference calculating means A8, and F/B correction amount calculating means A9 are used.

The numerical value converting means A7 calculates the upstream side exhaust air-fuel ratio AFup corresponding to the output current Irup based on the output current Irup of the upstream side air-fuel ratio sensor 40 and a map or calculation formula which defines the relationship between the output current Irup and the air-fuel ratio of the air-fuel ratio sensor 40. Therefore, the upstream side exhaust air-fuel ratio AFup corresponds to the air-fuel ratio of the exhaust gas flowing into the upstream side exhaust purification catalyst 20.

The air-fuel ratio difference calculating means A8 subtracts the target air-fuel ratio AFT calculated by the target air-fuel ratio setting means A6 from the upstream side exhaust air-fuel ratio AFup calculated by the numerical value converting means A7 to thereby calculate the air-fuel ratio difference DAF (DAF=AFup−AFT). This air-fuel ratio difference DAF is a value which expresses excess/deficiency of the amount of fuel fed with respect to the target air-fuel ratio AFT.

The F/B correction amount calculating means A9 processes the air-fuel ratio difference DAF calculated by the air-fuel ratio difference calculating means A8 by proportional integral derivative processing (PID processing) to thereby calculate the F/B correction amount DFi for compensating for the excess/deficiency of the amount of feed of fuel based on the following equation (1). The thus calculated F/B correction amount DFi is input to the fuel injection calculating means A3.

$$DFi = Kp \cdot DAF + Ki \cdot SDAF + Kd \cdot DDAF \quad (1)$$

Note that, in the above equation (1), Kp is a preset proportional gain (proportional constant), Ki is a preset integral gain (integral constant), and Kd is a preset derivative gain (derivative constant). Further, DDAF is the time derivative value of the air-fuel ratio difference DAF and is calculated by dividing the difference between the currently updated air-fuel ratio difference DAF and the previously updated air-fuel ratio difference DAF by the time corresponding to the updating interval. Further, SDAF is the time derivative value of the air-fuel ratio difference DAF. This time derivative value DDAF is calculated by adding the previously updated time derivative value DDAF and the currently updated air-fuel ratio difference DAF (SDAF=DDAF+DAF).

Note that, in the above embodiment, the air-fuel ratio of the exhaust gas flowing into the upstream side exhaust purification catalyst 20 is detected by the upstream side air-fuel ratio sensor 40. However, the precision of detection of the air-fuel ratio of the exhaust gas flowing into the upstream side exhaust purification catalyst 20 does not necessarily have to be high, and therefore, for example, the air-fuel ratio of the exhaust gas may be estimated based on the fuel injection amount from the fuel injector 11 and output of the air flow meter 39.

<Second Embodiment>

Next, referring to FIG. 17, a control system of an internal combustion engine according to a second embodiment of the present invention will be explained. The configuration of the control system of an internal combustion engine according to a second embodiment is basically similar to the configuration of the control system of an internal combustion engine according to the first embodiment. However, the control system of the present embodiment performs control of the air-fuel ratio different from the control in the first embodiment.

<Summary of Air-Fuel Ratio Control in Second Embodiment>

In the present embodiment, the target air-fuel ratio of the exhaust gas flowing into the upstream side exhaust purification catalyst 20 is set based on the output current Irdwn of the downstream side air-fuel ratio sensor 41 and the oxygen storage amount OSAsc of the upstream side exhaust purification catalyst 20. Specifically, when the output current Irdwn of the downstream side air-fuel ratio sensor 41 becomes the rich judged reference value Irrich or less, it is judged that the air-fuel ratio of the exhaust gas which is detected by the downstream side air-fuel ratio sensor 41 becomes the rich air-fuel ratio. In this case, the target air-fuel ratio is set to the lean set air-fuel ratio by the lean switching means, and then is maintained to this air-fuel ratio. The lean set air-fuel ratio is a predetermined air-fuel ratio which is leaner than the stoichiometric air-fuel ratio by a certain degree. For example, it is 14.65 to 20, preferably 14.68 to 18, more preferably 14.7 to 16 or so.

Then, if, in the state where the target air-fuel ratio is set to the lean set air-fuel ratio, the oxygen storage amount OSAsc of the upstream side exhaust purification catalyst 20 reaches a predetermined storage amount greater than zero, the target air-fuel ratio is switched to the weak lean set air-fuel ratio by the lean degree reducing means (note that, the oxygen storage amount at this time is referred to as the "lean degree change reference storage amount"). The weak lean set air-fuel ratio is a lean air-fuel ratio with a smaller difference from the stoichiometric air-fuel ratio than the lean set air-fuel ratio. For example, it is 14.62 to 15.7, preferably 14.63 to 15.2, more preferably 14.65 to 14.9 or so. Further, the lean degree change reference storage amount is the storage amount where the difference from zero is the predetermined change reference difference α.

On the other hand, when the output current Irdwn of the downstream side air-fuel ratio sensor 41 becomes zero (corresponding to a predetermined lean judged air-fuel ratio which is slightly leaner than the stoichiometric air-fuel ratio) or more, it is judged that the air-fuel ratio of the exhaust gas detected by the downstream side air-fuel ratio sensor 41 becomes the lean air-fuel ratio. In this case, the target air-fuel ratio is set to the rich set air-fuel ratio by the rich switching means. The rich set air-fuel ratio is a predetermined air-fuel ratio which is richer than the stoichiometric air-fuel ratio by a certain extent. For example, it is 10 to 14.55, preferably 12 to 14.52, more preferably 13 to 14.5 or so.

Then, in the state where the target air-fuel ratio is set to the rich set air-fuel ratio, if the oxygen storage amount OSAsc of the upstream side exhaust purification catalyst 20 reaches a predetermined storage amount which is smaller than the maximum storage amount, the target air-fuel ratio is switched to the weak rich set air-fuel ratio by the rich degree reducing means (Note that, the oxygen storage amount at this time means the "rich degree change reference storage amount"). The weak rich set air-fuel ratio is a rich air-fuel ratio with a smaller difference from the stoichiometric air-fuel ratio than the rich set air-fuel ratio. For example, it is 13.5 to 14.58, preferably 14 to 14.57, more preferably 14.3 to 14.55 or so. Further, the rich degree change reference storage amount is the storage amount where the difference from the maximum oxygen storage amount is the predetermined change reference difference α.

As a result, in the present embodiment, if the output current Irdwn of the downstream side air-fuel ratio sensor 41 becomes the rich judged reference value Irrich or less, first, the target air-fuel ratio is set to the lean set air-fuel ratio. Then, if the oxygen storage amount OSAsc becomes larger to a certain extent, the target air-fuel ratio is set to the weak lean set air-fuel ratio. Then, if the output current Irdwn of the downstream side air-fuel ratio sensor 41 becomes zero or more, first, the target air-fuel ratio is set to the rich set air-fuel ratio. Then, if the oxygen storage amount OSAsc becomes smaller to a certain extent, the target air-fuel ratio is set to the weak rich set air-fuel ratio, and then a similar operation is repeated.

<Explanation of Control Using Time Chart>

Figure 17:
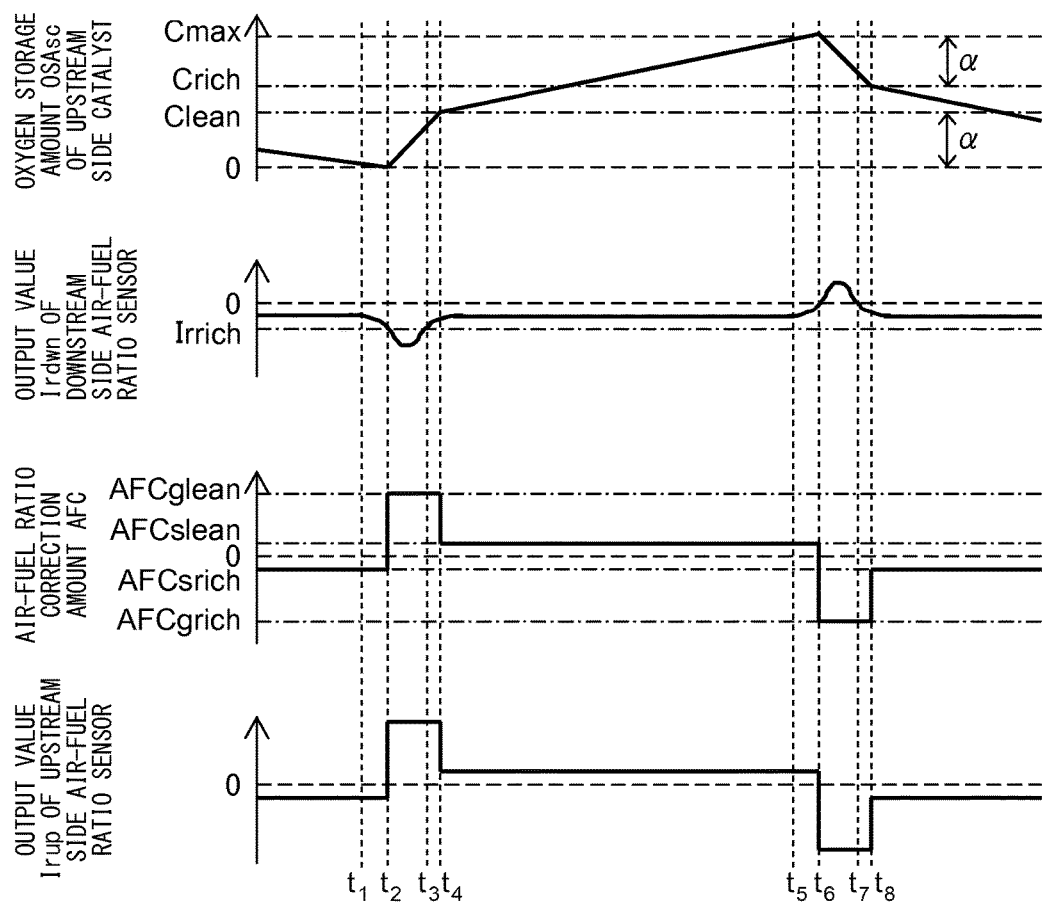
FIG. 17 is a time chart of the oxygen storage amount of the upstream side exhaust purification catalyst, etc.

Referring to FIG. 17, the above-mentioned operation will be specifically explained. FIG. 17 is a time chart of the oxygen storage amount OSAsc of the upstream side exhaust purification catalyst 20, etc., when performing air-fuel ratio control in the control system of an internal combustion engine according to the present embodiment.

In the illustrated example, in the state before the time $t_1$, the air-fuel ratio correction amount AFC of the target air-fuel ratio is set to the weak rich set correction amount AFCsrich. The weak rich set correction amount AFCsrich is a value corresponding to the weak rich set air-fuel ratio and a value smaller than 0. Therefore, the target air-fuel ratio of the exhaust gas flowing into the upstream side exhaust purification catalyst 20 is set to the rich air-fuel ratio. Along with this, the output current Irup of the upstream side air-fuel ratio sensor 40 becomes a negative value. The exhaust gas flowing into the upstream side exhaust purification catalyst 20 contains unburned gas, and therefore the oxygen storage amount OSAsc of the upstream side exhaust purification catalyst 20 gradually decreases. Note that, at this time, the unburned gas in the exhaust gas flowing into the upstream side exhaust purification catalyst 20 is oxidized and purified by the oxygen stored in the upstream side exhaust purification catalyst 20. For this reason, not only the amount of oxygen (and NOx), but also the amount of unburned gas exhausted from the upstream side exhaust purification catalyst 20 are suppressed.

If the oxygen storage amount OSAsc of the upstream side exhaust purification catalyst 20 gradually decreases, at the time $t_1$, the oxygen storage amount OSAsc decreases beyond the lower limit storage amount (see Clowlim of FIG. 13). If the oxygen storage amount OSAsc decreases more than the lower limit storage amount, part of the unburned gas flowing into the upstream side exhaust purification catalyst 20 flows out without being purified at the upstream side exhaust purification catalyst 20. For this reason, after the time $t_1$, along with the decrease of the oxygen storage amount OSAsc of the upstream side exhaust purification catalyst 20, the output current Irdwn of the downstream side air-fuel ratio sensor 41 gradually falls. Note that, unburned gas contained in the exhaust gas flowing out from the upstream side exhaust purification catalyst 20 is oxidized and purified by the downstream side exhaust purification catalyst 24.

Then, the output current Irdwn of the downstream side air-fuel ratio sensor 41 gradually falls and at the time $t_2$ reaches the rich judged reference value Irrich corresponding to the rich judged air-fuel ratio. In the present embodiment, if the output current Irdwn of the downstream side air-fuel ratio sensor 41 becomes the rich judgment reference value Irrich or less, the air-fuel ratio correction amount AFC is switched to the lean set correction amount AFCglean to suppress decrease of the oxygen storage amount OSAsc of the upstream side exhaust purification catalyst 20. The lean set correction amount AFCglean is a value which corresponds to the lean set air-fuel ratio and is a value which is larger than 0.

Note that, in the present embodiment, the air-fuel ratio shift amount AFC is switched after the output current Irdwn of the downstream side air-fuel ratio sensor 41 reaches the rich judged reference value Irrich, that is, after the air-fuel ratio of the exhaust gas flowing out from the upstream side exhaust purification catalyst 20 reaches the rich judged air-fuel ratio. This is because sometimes even if the oxygen storage amount of the upstream side exhaust purification catalyst 20 is sufficient, the air-fuel ratio of the exhaust gas flowing out from the upstream side exhaust purification catalyst 20 deviates very slightly from the stoichiometric air-fuel ratio. That is, if judging that the oxygen storage amount of the upstream side exhaust purification catalyst 20 has decreased over the lower limit storage amount even when the output current Irdwn slightly deviates from the value corresponding to the stoichiometric air-fuel ratio, there is the possibility that even though there is actually a sufficient oxygen storage amount, it will be judged that the oxygen storage amount OSAsc has decreased over the lower limit storage amount. Therefore, in the present embodiment, only after the air-fuel ratio of the exhaust gas flowing out from the upstream side exhaust purification catalyst 20 first reaches the rich judged air-fuel ratio, it is judged that the oxygen storage amount has decreased over the lower limit storage amount. Conversely speaking, the rich judged air-fuel ratio is set to an air-fuel ratio such that when the oxygen storage amount of the upstream side exhaust purification catalyst 20 is sufficient, the air-fuel ratio of the exhaust gas flowing out from the upstream side exhaust purification catalyst 20 will almost never be reached. Note that, the same can be said for the later explained lean judged air-fuel ratio.

If, at the time $t_2$, the target air-fuel ratio of the exhaust gas flowing into the upstream side exhaust purification catalyst 20 is switched to the lean set air-fuel ratio, the air-fuel ratio of the exhaust gas flowing into the upstream side exhaust purification catalyst 20 also changes from the rich air-fuel ratio to a lean air-fuel ratio. If, at the time $t_2$, the air-fuel ratio of the exhaust gas flowing into the upstream side exhaust purification catalyst 20 changes to the lean air-fuel ratio, the output current Irup of the upstream side air-fuel ratio sensor 40 becomes a positive value, and the oxygen storage amount OSAsc of the upstream side exhaust purification catalyst 20 starts to increase.

Note that, in the illustrated example, right after switching to the target air-fuel ratio, the output current Irdwn of the downstream side air-fuel ratio sensor 41 falls. This is because a delay arises from when switching the target air-fuel ratio to when the exhaust gas reaches the upstream side exhaust purification catalyst 20, and unburned gas flows out from the upstream side exhaust purification catalyst 20.

Then, along with the increase in the oxygen storage amount OSAsc of the upstream side exhaust purification catalyst 20, the air-fuel ratio of the exhaust gas flowing out from the upstream side exhaust purification catalyst 20 changes to the stoichiometric air-fuel ratio, and the output current Irdwn of the downstream side air-fuel ratio sensor 41 also becomes larger. Therefore, the output current Irdwn of the downstream side air-fuel ratio sensor 41 becomes larger than the rich judged reference value Irrich, after the time $t_3$. During this time as well, the air-fuel ratio correction amount AFC of the target air-fuel ratio is maintained at the lean set correction amount AFCglean, and the output current Irup of the upstream side air-fuel ratio sensor 40 is maintained at a positive value.

If the oxygen storage amount OSAsc of the upstream side exhaust purification catalyst 20 continues increasing, at the time $t_4$, it reaches the lean degree change reference storage amount Clean. In the present embodiment, if the oxygen storage amount OSAsc of the upstream side exhaust purification catalyst 20 becomes the lean degree change reference storage amount Clean or more, the air-fuel ratio correction amount AFC is switched to the weak lean set correction amount AFCslean so as to delay the increase in the oxygen storage amount OSAsc of the upstream side exhaust purification catalyst 20. The weak lean set correction amount AFCslean is a value which corresponds to the weak lean set air-fuel ratio and is smaller than AFCglean and larger than 0.

If, at the time $t_4$, the target air-fuel ratio is switched to the weak lean set air-fuel ratio, the difference of air-fuel ratio of the exhaust gas flowing into the upstream side exhaust purification catalyst 20 from the stoichiometric air-fuel ratio also becomes smaller. Along with this, the value of the output current Irup of the upstream side air-fuel ratio sensor 40 becomes smaller, and the speed of increase of the oxygen storage amount OSAsc of the upstream side exhaust purification catalyst 20 falls. Note that, the oxygen and $NO_X$ which flow into the upstream side exhaust purification catalyst 20 are stored and purified in the upstream side exhaust purification catalyst 20, respectively. For this reason, not only the amount of unburned gas exhausted from the upstream side exhaust purification catalyst 20, but also the amount of $NO_X$ exhausted is suppressed.

After the time $t_4$, the oxygen storage amount OSAsc of the upstream side exhaust purification catalyst 20 gradually increases, while speed of increase is slow. If the oxygen storage amount OSAsc of the upstream side exhaust purification catalyst 20 gradually increases, at the time $t_5$, the oxygen storage amount OSAsc increases beyond the upper limit storage amount (see Cuplim in FIG. 13). If the oxygen storage amount OSAsc increases beyond the upper limit storage amount, part of the oxygen flowing into the upstream side exhaust purification catalyst 20 flows out without being stored in the upstream side exhaust purification catalyst 20. For this reason, after the time $t_5$, along with the increase of the oxygen storage amount OSAsc of the upstream side exhaust purification catalyst 20, the output current Irdwn of the downstream side air-fuel ratio sensor 41 gradually rises. Note that, along with the upstream side exhaust purification catalyst 20 no longer storing part of the oxygen, $NO_X$ also is no longer reduced and purified, but this $NO_X$ is reduced and purified by the downstream side exhaust purification catalyst 24.

Then, the output current Irdwn of the downstream side air-fuel ratio sensor 41 gradually rises and, at the time $t_6$, reaches zero corresponding to the lean judged air-fuel ratio. In the present embodiment, if the output current of the downstream side air-fuel ratio sensor 41 becomes zero or more, the air-fuel ratio correction amount AFC is switched to the rich set correction amount AFCgrich to suppress the increase in the oxygen storage amount OSAsc of the upstream side exhaust purification catalyst 20. The rich set correction amount AFCgrich is a value corresponding to the rich set air-fuel ratio, and is smaller than 0.

If, at the time $t_6$, switching the target air-fuel ratio of the exhaust gas flowing into the upstream side exhaust purification catalyst 20 to the rich set air-fuel ratio, the air-fuel ratio of the exhaust gas flowing into the upstream side exhaust purification catalyst 20 changes from the lean air-fuel ratio to the rich air-fuel ratio. If, at the time $t_6$, the air-fuel ratio of the exhaust gas flowing into the upstream side exhaust purification catalyst 20 changes to the rich air-fuel ratio, the output current Irup of the upstream side air-fuel ratio sensor 40 becomes a negative value, and the oxygen storage amount OSAsc of the upstream side exhaust purification catalyst 20 starts to decrease.

Then, along with the decrease of the oxygen storage amount OSAsc of the upstream side exhaust purification catalyst 20, the air-fuel ratio of the exhaust gas flowing out from the upstream side exhaust purification catalyst 20 changes to the stoichiometric air-fuel ratio and the output current Irdwn of the downstream side air-fuel ratio sensor 41 also becomes smaller. Therefore, the output current Irdwn of the downstream air-fuel ratio sensor 41 becomes zero or less, after the time $t_7$. During this period as well, the air-fuel ratio correction amount AFC of the target air-fuel ratio is maintained at the rich set correction amount AFCgrich, while the output current Irup of the upstream side air-fuel ratio sensor 40 is maintained at a negative value.

If the oxygen storage amount OSAsc of the upstream side exhaust purification catalyst 20 continues to decrease, it reaches the rich degree change reference storage amount Crich at the time $t_8$. In the present embodiment, if the oxygen storage amount OSAsc of the upstream side exhaust purification catalyst 20 becomes the rich degree change reference storage amount Crich or less, the air-fuel ratio correction amount AFC is switched to the weak rich set correction amount AFCsrich so as to delay the rate of decrease of the oxygen storage amount OSAsc of the upstream side exhaust purification catalyst 20. The weak rich set correction amount AFCsrich is a value corresponding to the weak rich set air-fuel ratio, and is a value larger than AFCgrich and smaller than 0.

If switching the target air-fuel ratio to a weak rich set air-fuel ratio at the time $t_8$, the difference of the air-fuel ratio of the exhaust gas flowing into the upstream side exhaust purification catalyst 20 from the stoichiometric air-fuel ratio also becomes smaller. Along with this, the value of the output current Irup of the upstream side air-fuel ratio sensor 40 becomes larger, and the speed of decrease of the oxygen storage amount OSAsc of the upstream side exhaust purification catalyst 20 falls. Note that, the unburned gas in the exhaust gas flowing into the upstream side exhaust purification catalyst 20 is oxidized and purified at the upstream side exhaust purification catalyst 20. For this reason, not only the amounts of exhaust of oxygen and $NO_X$, but also the amount of exhaust of unburned gas from the upstream side exhaust purification catalyst 20 is suppressed.

After the time $t_8$, the oxygen storage amount OSAsc of the upstream side exhaust purification catalyst 20 gradually decreases while the speed of decrease is slow. As a result, unburned gas starts to flow out from the upstream side exhaust purification catalyst 20. As a result, in the same way as the time $t_2$, the output current Irdwn of the downstream side air-fuel ratio sensor 41 reaches the rich judged reference value Irrich. After this, the same operation as the operation of the times $t_1$ to $t_8$ is repeated.

<Action and Effect in Control of Present Embodiment>

According to the air-fuel ratio control of the above-mentioned present embodiment, right after the target air-fuel ratio is changed from the rich air-fuel ratio to the lean air-fuel ratio at the time $t_2$ and right after the target air-fuel ratio is changed from the lean air-fuel ratio to the rich air-fuel ratio at the time $t_6$, the difference from the stoichiometric air-fuel ratio is large (that is, the rich degree or lean degree is large). For this reason, it is possible to quickly decrease the unburned gas which flowed out from the upstream side exhaust purification catalyst 20 at the time $t_2$ and the $NO_X$ which flowed out from the upstream side exhaust purification catalyst 20 at the time $t_6$. Therefore, the outflow of unburned gas and $NO_X$ from the upstream side exhaust purification catalyst 20 can be suppressed.

Further, according to the air-fuel ratio control of the present embodiment, at the time $t_2$, the target air-fuel ratio is set to the lean set air-fuel ratio, then after the outflow of unburned gas from the upstream side exhaust purification catalyst 20 stops and the oxygen storage amount OSAsc of the upstream side exhaust purification catalyst 20 recovers to a certain extent, at the time $t_4$, the target air-fuel ratio is switched to the weak lean set air-fuel ratio. By making the difference of the target air-fuel ratio from the stoichiometric air-fuel ratio smaller in this way, from the time $t_4$ to the time $t_5$, it is possible to slow the speed of increase of the oxygen storage amount OSAsc of the upstream side exhaust purification catalyst 20. Due to this, it is possible to lengthen the time interval from the time $t_4$ to the time $t_6$. As a result, it is possible to make the amount of outflow of $NO_X$ or unburned gas from the upstream side exhaust purification catalyst 20 per unit time decrease. Furthermore, according to the above air-fuel ratio control, at the time $t_5$, it is possible to keep small the amount of outflow when $NO_X$ flows out from the upstream side exhaust purification catalyst 20. Therefore, it is possible to suppress the outflow of $NO_X$ from the upstream side exhaust purification catalyst 20.

In addition, according to the air-fuel ratio control of the present embodiment, at the time $t_6$, the target air-fuel ratio is set to the rich set air-fuel ratio, then after the outflow of $NO_X$ (oxygen) from the upstream side exhaust purification catalyst 20 stops and the oxygen storage amount OSAsc of the upstream side exhaust purification catalyst 20 decreases by a certain extent, at the time $t_8$, the target air-fuel ratio is switched to the weak rich set air-fuel ratio. By reducing the difference of the target air-fuel ratio from the stoichiometric air-fuel ratio in this way, it is possible to slow the speed of decrease of the oxygen storage amount OSAsc of the upstream side exhaust purification catalyst 20 from the time $t_8$ to the time $t_1$. Due to this, it is possible to lengthen the time interval from the time $t_8$ to the time $t_1$. As a result, it is possible to make the amount of outflow of $NO_X$ or unburned gas from the upstream side exhaust purification catalyst 20 per unit time decrease. Furthermore, according to the air-fuel ratio control, at the time $t_1$, it is possible to keep small the amount of outflow when unburned gas flows out from the upstream side exhaust purification catalyst 20. Therefore, it is possible to suppress the outflow of unburned gas from the upstream side exhaust purification catalyst 20.

Furthermore, in the present embodiment as well, as explained above, absolute values of the lean judged air-fuel ratio can be accurately detected by the downstream side air-fuel ratio sensor 41. For this reason, it is suppressed that the timing of switching to the weak rich set correction amount AFCrich of the air-fuel ratio correction amount AFC becomes delayed and thus $NO_X$ flows out from the upstream side exhaust purification catalyst 20. In addition, it is possible to suppress switching at a timing at which switching is unnecessary.

Figure 18:
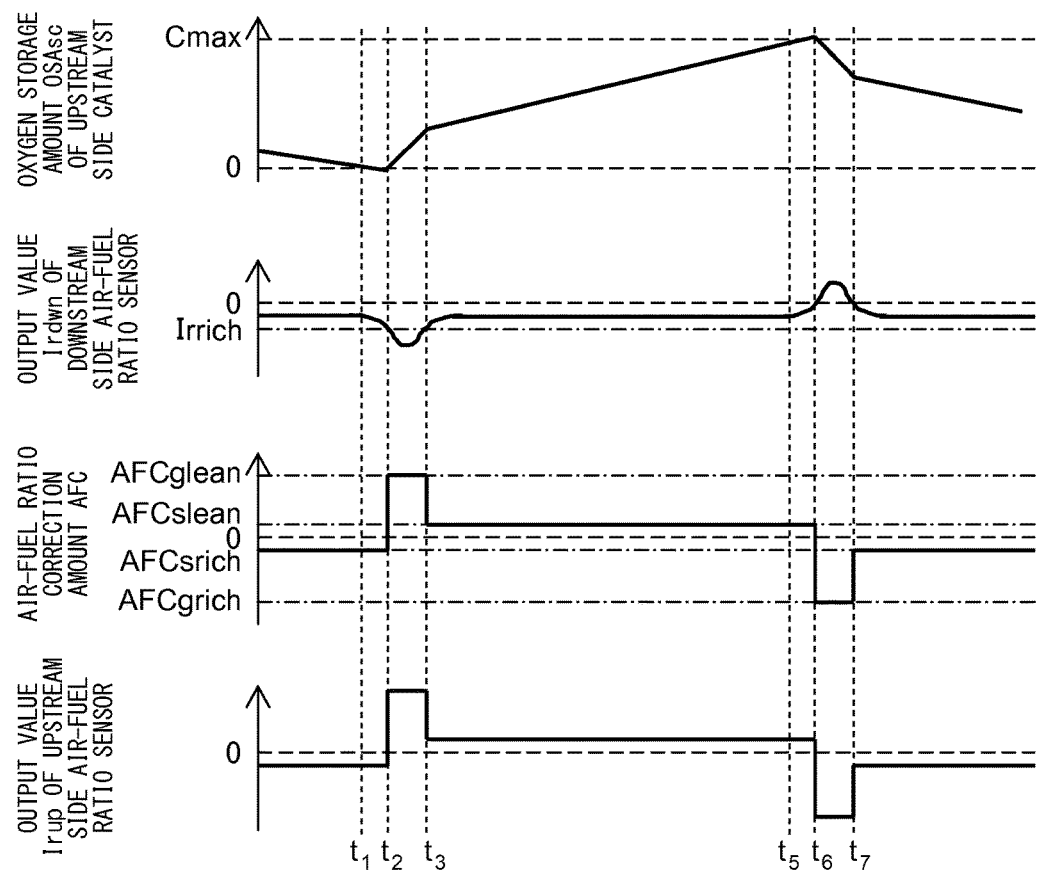
FIG. 18 is a time chart of the oxygen storage amount of the upstream side exhaust purification catalyst, etc.

Note that, in the above embodiment, when the oxygen storage amount OSAsc of the upstream side exhaust purification catalyst 20 becomes the lean degree change reference storage amount Clean or more, the target air-fuel ratio is changed so that the difference from the stoichiometric air-fuel ratio becomes smaller. However, the timing for changing the target air-fuel ratio so that the difference from the stoichiometric air-fuel ratio becomes smaller may be any time between the times $t_2$ to $t_6$. For example, as shown in FIG. 18, when the output current Irdwn of the downstream side air-fuel ratio sensor 41 becomes the rich judged reference value Irrich or more, the target air-fuel ratio may be changed so that the difference from the stoichiometric becomes smaller.

Similarly, in the above embodiment, when the oxygen storage amount OSAsc of the upstream side exhaust purification catalyst 20 becomes a rich degree change reference storage amount Crich or less, the target air-fuel ratio is changed so that the difference from the stoichiometric air-fuel ratio becomes smaller. However, the timing for changing the target air-fuel ratio so that the difference from the stoichiometric air-fuel ratio becomes smaller may be any time between the times $t_6$ to $t_2$. For example, as shown in FIG. 18, when the output current Irdwn of the downstream side air-fuel ratio sensor 41 becomes zero or less, the target air-fuel ratio may be changed so that the difference from the stoichiometric becomes smaller.

Furthermore, in the above embodiment, between the times $t_4$ and $t_6$ and between the times $t_8$ and $t_2$, the target air-fuel ratio is fixed at the weak lean set air-fuel ratio or weak rich set air-fuel ratio, respectively. However, during these time periods, the target air-fuel ratio may be set so that the difference becomes smaller in stages or may be set so that the difference becomes continuously smaller.

Expressing these together, according to the present invention, the ECU 31 can be said to comprise: an air-fuel ratio lean switching means for changing the target air-fuel ratio of the exhaust gas flowing into the upstream side exhaust purification catalyst 20 to the lean set air-fuel ratio when the output current of the downstream side air-fuel ratio sensor 41 becomes a value corresponding to a rich judged air-fuel ratio, which is richer than the stoichiometric air-fuel ratio, or less; a lean degree reducing means for changing the target air-fuel ratio to a lean air-fuel ratio with a smaller difference from the stoichiometric air-fuel ratio than the lean set air-fuel ratio after the air-fuel ratio lean switching means changes the target air-fuel ratio and before the output current of the downstream side air-fuel ratio sensor 41 becomes zero or more; an air-fuel ratio rich switching means for changing target air-fuel ratio to a rich set air-fuel ratio when the output current of the downstream side air-fuel ratio sensor 41 becomes zero or more; and a rich degree reducing means for changing the target air-fuel ratio to a rich air-fuel ratio with a smaller difference from the stoichiometric air-fuel ratio than the rich set air-fuel ratio, after the air-fuel ratio rich switching means changes the air-fuel ratio and before the output current of the downstream side air-fuel ratio sensor 41 becomes a value corresponding to the rich judged air-fuel ratio or less.

Note that, in this Description, it is explained that the oxygen storage amount of the exhaust purification catalyst changes between the maximum oxygen storage amount and zero. This means that the amount of oxygen which can be further stored by the exhaust purification catalyst changes between zero (when the oxygen storage amount is the maximum oxygen storage amount) and the maximum value (when the oxygen storage amount is zero).

REFERENCE SIGNS LIST 5. combustion chamber
6. intake valve
8. exhaust valve
10. spark plug
11. fuel injector
13. intake branch pipe
15. intake pipe
18. throttle valve
19. exhaust manifold
20. upstream side exhaust purification catalyst
21. upstream side casing
22. exhaust pipe
23. downstream side casing
24. downstream side exhaust purification catalyst
31. ECU
39. air flow meter
40. upstream side air-fuel ratio sensor
41. downstream side air-fuel ratio sensor

The invention claimed is:

1. A control system of an internal combustion engine comprising: an exhaust purification catalyst which is provided in an exhaust passage of an internal combustion engine and which is configured to store oxygen, a downstream side air-fuel ratio sensor which is provided at a downstream side, in the direction of flow of exhaust, from said exhaust purification catalyst in said exhaust passage, and an engine control device which controls the internal combustion engine in accordance with the output of said downstream side air-fuel ratio sensor, wherein said downstream side air-fuel ratio sensor is configured so that an applied voltage, in which an output current becomes zero, changes in accordance with the exhaust air-fuel ratio and so that when the exhaust air-fuel ratio is a stoichiometric air-fuel ratio, if increasing the applied voltage at said downstream side air-fuel ratio sensor, the output current increases along with that, and when said downstream air-fuel ratio sensor detects the air-fuel ratio of the exhaust gas, the applied voltage at said downstream side air-fuel ratio sensor is fixed to a constant voltage, and said constant voltage is the voltage in which the output current becomes zero when the exhaust air-fuel ratio is an air-fuel ratio which is leaner than the stoichiometric air-fuel ratio.

2. The control system of an internal combustion engine according to claim 1, wherein said engine control device judges that the exhaust air-fuel ratio is said predetermined air-fuel ratio when the output current of said downstream side air-fuel ratio sensor becomes zero.

3. The control system of an internal combustion engine according to claim 1, further comprising an upstream side air-fuel ratio sensor which is provided at an upstream side, in the direction of flow of exhaust, from said exhaust purification catalyst in said exhaust passage,
wherein said engine control device controls the air-fuel ratio of the exhaust gas flowing into said exhaust purification catalyst so that the air-fuel ratio detected by said upstream side air-fuel ratio sensor becomes the target air-fuel ratio.

4. The control system of an internal combustion engine according to claim 3, wherein
said upstream side air-fuel ratio sensor is configured so that an applied voltage, in which an output current becomes zero, changes in accordance with the exhaust air-fuel ratio, and so that when the exhaust air-fuel ratio is a stoichiometric air-fuel ratio, if increasing the applied voltage at said upstream side air-fuel ratio sensor increase, the output current increases along with that, and when said upstream air-fuel ratio sensor detects the air-fuel ratio of the exhaust gas, the applied voltage at said upstream side air-fuel ratio sensor is fixed to a constant voltage, and said constant voltage is the voltage in which the output current becomes zero when the exhaust air-fuel ratio is the stoichiometric air-fuel ratio.

5. The control system of an internal combustion engine according to claim 3, wherein
said upstream side air-fuel ratio sensor is configured so that an applied voltage, in which an output current becomes zero, changes in accordance with the exhaust air-fuel ratio, and so that when the exhaust air-fuel ratio is a stoichiometric air-fuel ratio, if increasing the applied voltage at said upstream side air-fuel ratio sensor, the output current increases along with that, and
the applied voltage at said downstream side air-fuel ratio sensor is lower than the applied voltage of said upstream side air-fuel ratio sensor.

6. The control system of an internal combustion engine according to claim 3, wherein said engine control device makes the target air-fuel ratio of the exhaust gas flowing into said exhaust purification catalyst, richer than the stoichiometric air-fuel ratio, when the output current of said upstream side air-fuel ratio sensor becomes zero or more.

7. The control system of an internal combustion engine according to claim 6, wherein said engine control device comprises:

an oxygen storage amount increasing means for continuously or intermittently making a target air-fuel ratio of exhaust gas flowing into said exhaust purification catalyst leaner than the stoichiometric air-fuel ratio, when the output current of said downstream side air-fuel ratio sensor becomes a value which corresponds to a rich judged air-fuel ratio, which is richer than the stoichiometric air-fuel ratio, or less, until the oxygen storage amount of said exhaust purification catalyst becomes a predetermined storage amount which is smaller than the maximum oxygen storage amount; and an oxygen storage amount decreasing means for continuously or intermittently making said target air-fuel ratio richer than the stoichiometric air-fuel ratio, when the oxygen storage amount of said exhaust purification catalyst becomes said predetermined storage amount or more, so that the oxygen storage amount never reaches the maximum oxygen storage amount but decreases toward zero.

8. The control system of an internal combustion engine according to claim 6, wherein said engine control device comprises:

an air-fuel ratio lean switching means for making the target air-fuel ratio of the exhaust gas flowing into said exhaust purification catalyst change to a lean set air-fuel ratio which is leaner than the stoichiometric air-fuel ratio, when the output current of said downstream side air-fuel ratio sensor becomes a value which corresponds to a rich judged air-fuel ratio, which is richer than the stoichiometric air-fuel ratio, or less, a lean degree reducing means for making said target air-fuel ratio change to a lean air-fuel ratio with a smaller difference from said stoichiometric air-fuel ratio than the lean set air-fuel ratio, after said air-fuel ratio lean switching means makes said target air-fuel ratio change and before the output current of said downstream side air-fuel ratio sensor becomes zero or more, an air-fuel ratio rich switching means for making said target air-fuel ratio change to a rich set air-fuel ratio which is richer than the stoichiometric air-fuel ratio, when the output current of said downstream side air-fuel ratio sensor becomes zero or more, and a rich degree reducing means for making said target air-fuel ratio change to a rich air-fuel ratio with a smaller difference from said stoichiometric air-fuel ratio than the rich set air-fuel ratio, after said air-fuel ratio rich switching means makes said target air-fuel ratio change and before the output current of said downstream side air-fuel ratio sensor becomes a value which corresponds to said rich judged air-fuel ratio or less.

9. The control system of an internal combustion engine according to claim 1, wherein
said downstream side air-fuel ratio sensor comprises:
a first electrode which is exposed through a diffusion regulating layer to exhaust gas for which the air-fuel ratio is to be detected;
a second electrode which is exposed to a reference atmosphere, a solid electrolyte layer which is arranged between said first electrode and said second electrode; and
a voltage application device which applies voltage across said first electrode and said second electrode, said applied voltage being the voltage which is applied by the voltage application device, said downstream side air-fuel ratio sensor is configured so as to have, for each exhaust air-fuel ratio,
a current increase region which is a voltage region where the output current increases along with an increase in the applied voltage; and
a current fine increase region which is a voltage region where an amount of increase of the output current with respect to an amount of increase of the applied voltage becomes smaller than said current increase region due to provision of said diffusion regulating layer, and
the constant voltage at said downstream side air-fuel ratio sensor is a voltage within said current fine increase region when the exhaust air-fuel ratio is the stoichiometric air-fuel ratio.

10. The control system of an internal combustion engine according to claim 1, wherein
said downstream side air-fuel ratio sensor is configured so as to have, for each exhaust air-fuel ratio, a limit current region which is a voltage region where said output current becomes a limit current, and
the constant voltage of said downstream side air-fuel ratio sensor is a voltage within said limit current region when the exhaust air-fuel ratio is the stoichiometric air-fuel ratio.

11. The control system of an internal combustion engine according to claim 1, wherein
said downstream side air-fuel ratio sensor is configured to have, for each exhaust air-fuel ratio, in the relationship between said applied voltage and output current,
a proportional region which is a voltage region where the output current increases in proportion to an increase of the applied voltage;
a moisture breakdown region which is a voltage region where the output current changes in accordance with a change of the applied voltage due to the breakdown of moisture; and
a middle region which is a voltage region between these proportional region and moisture breakdown region, and
said constant voltage at the downstream side air-fuel ratio sensor is a voltage within said middle region when the exhaust air-fuel ratio is the stoichiometric air-fuel ratio.

12. The control system of an internal combustion engine according to claim 1, wherein said constant voltage at the downstream side air-fuel ratio sensor is larger than a voltage in which the output current becomes zero when the exhaust air-fuel ratio is 1% higher than the stoichiometric air-fuel ratio, and is lower than a voltage in which the output current becomes zero when the exhaust air-fuel ratio is the stoichiometric air-fuel ratio.

13. The control system of an internal combustion engine according to claim 1, wherein
said downstream side air-fuel ratio sensor is configured so that, for each exhaust air-fuel ratio, in the relationship between said applied voltage and output current, the output current increases up to a first curved point as the applied voltage increases, the output current increases from the first curved point to a second curved point as the applied voltage increases, the output current increases from the second curved point as the applied voltage increases, and, in the voltage region between the first curved point and the second curved point, the amount of increase of the output current with respect to an amount of increase in the applied voltage becomes smaller than in other voltage regions, and
the constant voltage at said downstream side air-fuel ratio sensor is set to a voltage between said first curved point and said second curved point when the exhaust air-fuel ratio is the stoichiometric air-fuel ratio.

14. The control system of an internal combustion engine according to claim 1, wherein
said downstream side air-fuel ratio sensor comprises:
a first electrode which is exposed through a diffusion regulating layer to exhaust gas for which the air-fuel ratio is to be detected;
a second electrode which is exposed to a reference atmosphere;
a solid electrolyte layer which is arranged between said first electrode and said second electrode; and
a voltage application device which applies voltage across said first electrode and said second electrode, said diffusion regulating layer being formed by alumina, said applied voltage being the voltage which is applied by the voltage application device, and
said constant voltage at said downstream side air-fuel ratio sensor is set to voltage not lower than 0.1V and lower than 0.45V.

15. The control system of an internal combustion engine according to claim 3, wherein
said upstream side air-fuel ratio sensor comprises:
a first electrode which is exposed through a diffusion regulating layer to exhaust gas for which the air-fuel ratio is to be detected;
a second electrode which is exposed to a reference atmosphere;
a solid electrolyte layer which is arranged between said first electrode and said second electrode; and
a voltage application device which applies voltage across said first electrode and said second electrode, said diffusion regulating layer being formed by alumina, said applied voltage being the voltage which is applied by the voltage application device, and
said constant voltage at said upstream side air-fuel ratio sensor is set to a voltage not lower than 0.4V and not higher than 0.45V.

16. The control system of an internal combustion engine according to claim 1, wherein
said downstream side air-fuel ratio sensor comprises:
a first electrode which is exposed through a diffusion regulating layer to exhaust gas for which the air-fuel ratio is to be detected;
a second electrode which is exposed to a reference atmosphere;
a solid electrolyte layer which is arranged between said first electrode and said second electrode;
a voltage application device which applies voltage across said first electrode and said second electrode; and
a current detection device which detects the current flowing across said first electrode and said second electrode, said applied voltage being the voltage which is applied by the voltage application device, and said output current being the current which is detected by said current detection device.

* * * * *